(12) United States Patent
Flower

(10) Patent No.: US 10,285,603 B2
(45) Date of Patent: *May 14, 2019

(54) QUANTIFICATION OF ABSOLUTE BLOOD FLOW IN TISSUE USING FLUORESCENCE MEDIATED PHOTOPLETHYSMOGRAPHY

(71) Applicant: Novadaq Technologies ULC, Burnaby (CA)

(72) Inventor: Robert W. Flower, Hunt Valley, MD (US)

(73) Assignee: NOVADAQ TECHNOLOGIES ULC, Burnaby (CA)

(*) Notice: Subject to any disclaimer, the term of this patent is extended or adjusted under 35 U.S.C. 154(b) by 310 days.

This patent is subject to a terminal disclaimer.

(21) Appl. No.: 14/305,950

(22) Filed: Jun. 16, 2014

(65) Prior Publication Data

US 2014/0371583 A1    Dec. 18, 2014

Related U.S. Application Data

(60) Provisional application No. 61/835,408, filed on Jun. 14, 2013.

(51) Int. Cl.
*A61B 5/0275* (2006.01)
*A61B 5/00* (2006.01)
*A61B 5/0295* (2006.01)

(52) U.S. Cl.
CPC .......... *A61B 5/0275* (2013.01); *A61B 5/0071* (2013.01); *A61B 5/0295* (2013.01); *A61B 5/6826* (2013.01)

(58) Field of Classification Search
CPC ... A61B 5/0275; A61B 5/0261; A61B 5/0071; A61B 5/0295; A61B 5/6826

USPC .................................................. 600/431
See application file for complete search history.

(56) References Cited

U.S. PATENT DOCUMENTS

| | | |
|---|---|---|
| 6,577,884 B1 | 6/2003 | Boas |
| 7,474,906 B2 | 1/2009 | Rubinstein et al. |
| 8,285,353 B2 | 10/2012 | Choi et al. |
| 8,718,747 B2 | 5/2014 | Bjørnerud et al. |
| 9,451,903 B2 | 9/2016 | Feinberg |
| 2002/0007123 A1 | 1/2002 | Balas |

(Continued)

FOREIGN PATENT DOCUMENTS

| | | |
|---|---|---|
| JP | 2008-532682 A | 8/2008 |
| JP | 2008-220926 A | 9/2008 |

(Continued)

OTHER PUBLICATIONS

Alm, A. et al. (1973). "Ocular and Optic Nerve Blood Flow at Normal and Increased Intraocular Pressures in Monkeys (*Macaca irus*): A Study with Radioactively Labelled Microspheres including Flow Determinations in Brain and Some Other Tissues," *Experimental Eye Research* 15:15-29.

(Continued)

*Primary Examiner* — Amanda Lauritzen Moher
*Assistant Examiner* — Katherine M McDonald
(74) *Attorney, Agent, or Firm* — Morrison & Foerster LLP

(57) ABSTRACT

There is provided a method and a system for quantification of absolute blood flow in tissue using near-infrared fluorescence angiography in conjunction with photoplethysmography (fluorescence-mediated photoplethysmography). The method and system of the present invention provide absolute, real-time measurements of flow in terms of volume/time/area based upon measurement of fluorescence intensity.

11 Claims, 21 Drawing Sheets

(56) References Cited

U.S. PATENT DOCUMENTS

| | | |
|---|---|---|
| 2003/0127609 A1 | 7/2003 | El Hage et al. |
| 2005/0065432 A1 | 3/2005 | Kimura |
| 2006/0011853 A1 | 1/2006 | Spartiotis et al. |
| 2008/0188728 A1 | 8/2008 | Neumann et al. |
| 2008/0221421 A1 | 9/2008 | Choi et al. |
| 2009/0112097 A1 | 4/2009 | Kato et al. |
| 2010/0080757 A1 | 4/2010 | Haaga et al. |
| 2012/0323118 A1 | 12/2012 | Menon Gopalakrishna et al. |
| 2014/0254909 A1 | 9/2014 | Carmi et al. |
| 2014/0371583 A1 | 12/2014 | Flower |
| 2015/0112192 A1 | 4/2015 | Docherty et al. |
| 2015/0164396 A1 | 6/2015 | Acharya et al. |
| 2015/0182137 A1 | 7/2015 | Flower et al. |
| 2015/0248758 A1 | 9/2015 | Pautot |
| 2016/0253800 A1 | 9/2016 | Gurevich et al. |
| 2017/0084024 A1 | 3/2017 | Gurevich |
| 2017/0245766 A1 | 8/2017 | Flower et al. |

FOREIGN PATENT DOCUMENTS

| | | |
|---|---|---|
| WO | WO-90/12537 A1 | 11/1990 |
| WO | WO-2015/001427 A2 | 1/2015 |

OTHER PUBLICATIONS

Eren, S. et al. (Dec. 1995). "Assessment of Microcirculation of an Axial Skin Flap Using Indocyanine Green Fluorescence Angiography," *Plastic and Reconstructive Surgery* 96(7):1636-1649.

Flower, R.W. (Dec. 1973). "Injection Technique for Indocyanine Green and Sodium Fluorescein Dye Angiography of the Eye," *Investigative Ophthalmology* 12:881-895.

Flower, R.W. et al. (Aug. 1977). "Quantification of Indicator Dye Concentration in Ocular Blood Vessels," *Exp. Eye Res.* 25(2):103-111.

Nadler, S.B. et al. (Feb. 1962). "Prediction of Blood Volume In Normal Human Adults," *Surgery* 51(2):224-232.

Nunan, R. et al. (2014). "Clinical Challenges of Chronic Wounds: Searching for an Optimal Animal Model to Recapitulate their Complexity," *The Company of Biologists—Disease Models & Mechanisms* 7:1205-1213.

Stadler, I. et al. (Jul.-Aug. 2004). "Development of a simple, noninvasive, clinically relevant model of pressure ulcers in the mouse," *Journal of Investigative Surgery* 17(4):221-227.

U.S. Appl. No. 15/013,945, filed Feb. 2, 2016, by Gurevich et al. (Copy not attached).

Humphreys, Kenneth, et al., "Noncontact simultaneous dual wavelength photoplethysmogrphy: A further step toward noncontact pulse oximetry," Review of Scientific Instruments 78, 044304, 88 pgs. (2007).

Feb. 5, 2015 PCT Written Opinion of the International Searching Authority and PCT International Search Report.

Elgendi, M., "On the Analysis of Fingertip Photoplethysmogram Signals", Current Cardiology Reviews, 2012, vol. 8, No. 1, pp. 14-25.

Jayanthy, A.K. et al., "Measuring Blood Flow: Techniques and Applications—A Review", IJRRAS, vol. 6, No. 2, pp. 203-216, Feb. 2011.

Canadian Office Action dated Nov. 4, 2016 for Canadian Patent application No. 2,913,692 filed on Jun. 16, 2014, five pages.

European Supplementary Partial Search Report dated Jan. 20, 2017 for EP Application No. 14820367.0, filed on Nov. 25, 2015, seven pages.

International Search Report and Written Opinion dated Dec. 28, 2016 for International Application No. PCT/IB2016/001216 filed on Jul. 29, 2016, eight pages.

Japanese Office Action dated Nov. 14, 2016 for Japanese Patent Application No. 2016-518598 filed on Dec. 9, 2015, five pages.

U.S. Non Final Office Action dated Sep. 28, 2016, for U.S. Appl. No. 14/510,848, filed Oct. 9, 2014, twenty pages.

U.S. Appl. No. 15/224,088, filed Jul. 29, 2016, by Gurevich et al. (Copy not attached).

U.S. Appl. No. 15/433,502, filed Feb. 15, 2017, by Flower et al. (Copy not attached).

Australian Office Action dated Jun. 28, 2018 for Australian Patent Application No. 2016325592 filed on Mar. 21, 2018, four pages.

Canadian Office Action dated Aug. 14, 2018 for Canadian Patent application No. 2,913,692 filed on Nov. 26, 2015, three pages.

International Preliminary Report on Patentability dated Apr. 5, 2018 for International Application No. PCT/IB2016/001216 filed on Jul. 29, 2016, six pages.

International Preliminary Report on Patentability dated Aug. 30, 2018 for International Application No. PCT/CA2017/050189 filed on Feb. 15, 2017, seven pages.

Japanese Notice of Allowance dated Feb. 16, 2018 for Japanese Patent Application No. 2016-518598 filed on Dec. 9, 2015, six pages.

Korean Office Action dated Jun. 27, 2018 for KR Application No. 10-2016-7000943 filed on Jan. 13, 2016, four pages.

U.S. Final Office Action dated Jul. 20, 2018, for U.S. Appl. No. 15/224,088, filed Jul. 29, 2016, seven pages.

U.S. Non Final Office Action dated Feb. 23, 2018, for U.S. Appl. No. 15/224,088, filed Jul. 29, 2016, nineteen pages.

U.S. Non Final Office Action dated Jun. 28, 2018, for U.S. Appl. No. 14/510,848, filed Oct. 9, 2014, eighteen pages.

U.S. Non Final Office Action dated Sep. 17, 2018, for U.S. Appl. No. 15/433,502, filed Feb. 15, 2017, eleven pages.

Maarek et al. (Mar. 1, 2007). "Fluorescence Dilution Technique for Measurement of Cardiac Output and Circulating Blood Volume in Healthy Human Subjects," *Anesthesiology* 106(3):491-498.

Mitra et al. (Sep. 1, 2003). "Serial Determinations of Absolute Plasma Volume with Indocyanine Green During Hemodialysis," *Journal of American Society of Nephrology (JASN)* 14:2345-2351.

Canadian Office Action dated Aug. 28, 2017 for Canadian Patent application No. 2,913,692 filed on Nov. 26, 2015, three pages.

European Communication Pursuant to Rules 70(2) and 70a(2) EPC dated May 23, 2017 for EP Application No. 14820367.2, filed on Nov. 25, 2015, one page.

European Extended Search Report dated May 4, 2017 for EP Application No. 14820367.2, filed on Nov. 25, 2015, ten pages.

International Search Report and Written Opinion dated May 11, 2017, for International Application No. PCT/CA2017/050189, filed on Feb. 15, 2017, eleven pages.

Japanese Office Action dated Jun. 30, 2017 for JP Application No. 2016-518598, filed on Dec. 9, 2015, four pages.

Korean Office Action dated Oct. 19, 2017 for KR Application No. 10-2016-7000943 filed on Jan. 13, 2016, ten pages.

U.S. Final Office Action dated Jun. 22, 2017, for U.S. Appl. No. 14/510,848, filed Oct. 9, 2014, fourteen pages.

A  B  C

Figure 3
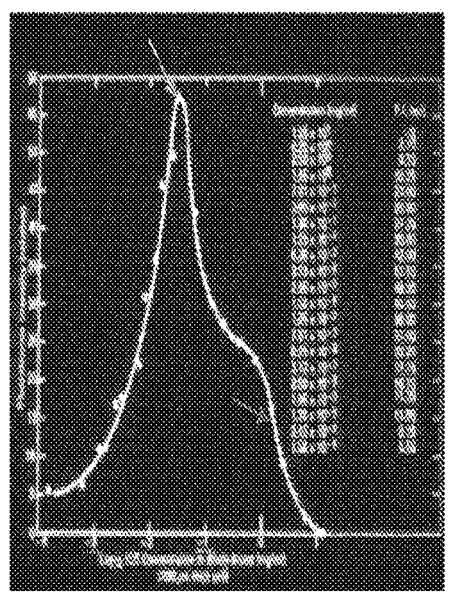
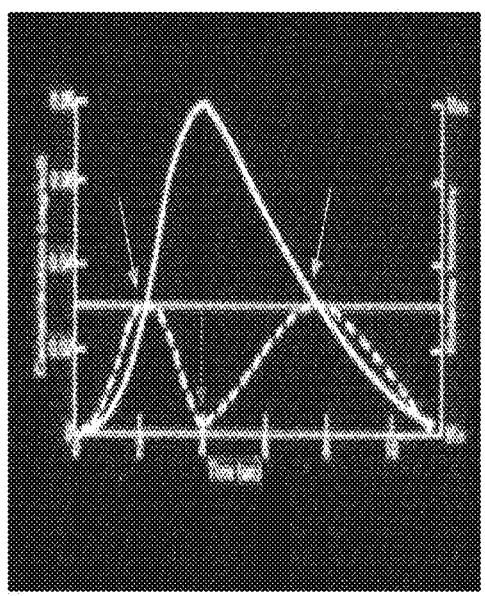
A　　　　　　　　B

Figure 4
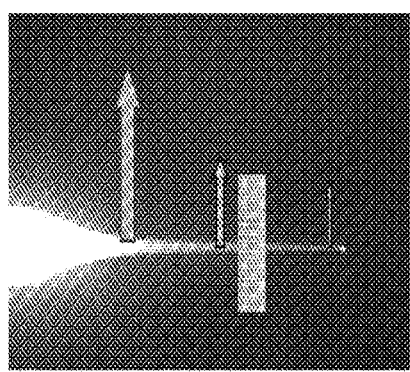 A
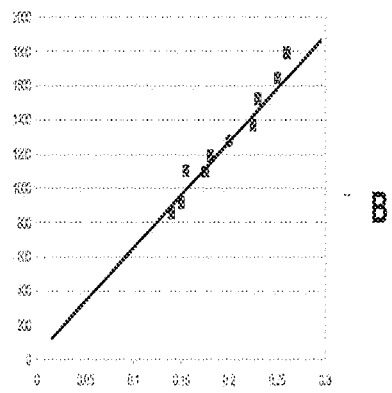 B

Figure 21
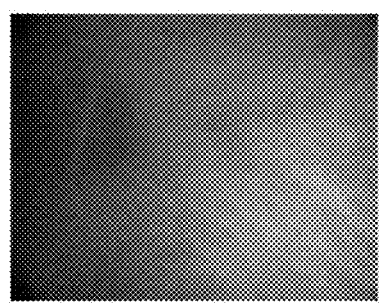 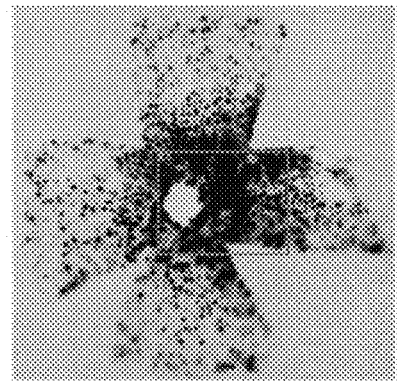
A B

QUANTIFICATION OF ABSOLUTE BLOOD FLOW IN TISSUE USING FLUORESCENCE MEDIATED PHOTOPLETHYSMOGRAPHY

CROSS-REFERENCE TO RELATED APPLICATION

This application claims the benefit of priority of U.S. Provisional Application No. 61/835,408 filed Jun. 14, 2013, the disclosure of which is incorporated herein by reference.

TECHNICAL FIELD

The present invention relates generally to the field of optical assessment of blood perfusion in tissue, and particularly to quantitative assessment of absolute blood perfusion in tissue.

BACKGROUND

Quantification of tissue (e.g., skin) blood perfusion assessment continues to be of fast-growing interest amongst clinicians, with applications across many surgical and non-surgical specialties. Although simple binary assessment (flow versus no-flow) may be adequate for some clinic al applications, frequently, quantification relative to some standard is needed for many other clinical applications. Increasingly, quantification in absolute terms (e.g., volume/time as a measurement of flow) is of interest. However, quantitative assessment of absolute blood perfusion in tissue as a tool of clinical assessment has been elusive.

Photoplethysmography (PPG) is an optical technique used to detect blood volume changes in the microvasculature. The observed waveform in PPG correlates with heartbeat, and PPG-based technology has been deployed in commercially available medical devices for measuring parameters such as oxygen saturation, blood pressure and cardiac output.

Despite the relatively wide deployment of medical devices based on PPG detection, PPG has not been exploited to facilitate routine determination of absolute measurement of tissue blood perfusion. A methodology with such capabilities would be of significant value to clinicians, since it would make possible routine acquisition of tissue blood perfusion measurements having the dimensions of volume/time/area. Only measurements having such dimensions allow for valid, direct inter-site and inter-subject comparisons. Therefore, there is a need for methods and systems for quantitative assessment of absolute blood perfusion in tissue.

SUMMARY

In accordance with one aspect of the invention, there is provided a method for determining aggregate flow of blood through vasculature in a tissue of interest such as for example skin tissue. The method includes measuring a cross-sectional area of a tissue volume end, measuring a thickness increase of a blood volume layer, determining a pulse duty cycle, determining a duration of a single blood pressure pulse, and deriving the aggregate blood flow, F, according to the inequality F=(A) (ΔL) ($P_{DC}$)/Δt. In the inequality F, ΔV=(cross-sectional area of the tissue volume end, A)×(thickness increase, ΔL, of the blood volume layer, L), $P_{DC}$ is the pulse duty cycle and Δt=duration of a single pressure pulse.

In further aspects, the method includes a fluorescence imaging protocol which includes administering an appropriate volume of a fluorescence dye into the vasculature supplying the tissue area of interest, and obtaining a sequence of angiographic images of the tissue area of interest. In further aspects, the fluorescence dye is ICG, which is administered at a concentration of between about 25-50 mg/mL. In yet further aspects, the angiographic images are obtained at a frame rate of 20-30 frames per second, and such images are obtained by a near-infrared fluorescence imaging system. In various aspects, the imaging system includes a laser for excitation of the ICG and a camera for capturing images of the fluorescence emitted by the ICG.

In accordance with another aspect of the invention, there is provided a method for quantifying absolute blood flow through a tissue volume. The method includes administering an appropriate volume of a fluorescence dye into vasculature supplying the tissue volume, obtaining a sequence of angiographic images of the tissue volume, calculating average fluorescence intensities for the sequence of angiographic images of the tissue volume, and generating a plot of time-varying average fluorescence intensity. In various aspects, the fluorescence dye is indocyanine green (ICG), and the ICG is administered at a concentration of between about 25-50 mg/mL, and the tissue volume comprises skin tissue. In various further aspects, the angiographic images are obtained at a frame rate of about 20-30 frames per second, and in further aspects, the angiographic images are obtained by a near-infrared fluorescence imaging system. In various aspects, the imaging system includes a laser for excitation of the ICG and a camera for capturing images of the fluorescence emitted by the ICG.

BRIEF DESCRIPTION OF THE DRAWINGS

In accompanying drawings which illustrate embodiments of the invention,

FIG. 3A-3B schematically represent the time-varying relationship between indocyanine green (ICG) concentration and fluorescence intensity during transit of ICG through a blood vessel;

FIG. 4A-4B show a fluorescence image of a tapered capillary tube containing a 0.03 mg/ml concentration ICG solution and a graph of the resulting linear relationship between capillary diameter and fluorescence intensity;

FIG. 21A-21B show an image from the human eye angiogram (21A) and the retinal area represented as a box superimposed upon the autoradiograph of a flat-mounted choroid from the left eye of one of the monkeys (21B) used by Alm and Bill as described in the specification.

DETAILED DESCRIPTION

Reference will now be made in detail to implementations and embodiments of various aspects and variations of the invention, examples of which are illustrated in the accompanying drawings.

Figure 1:
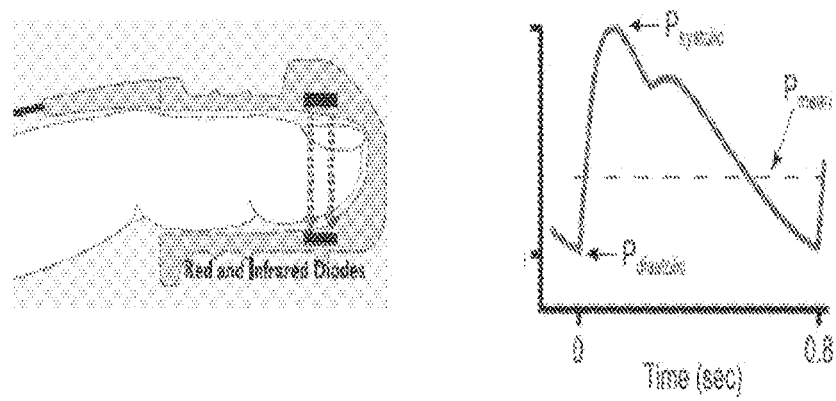
FIG. 1 illustrates measurement of aggregate fingertip blood volume during a single blood pressure pulse using conventional photoplethysmography (PPG)

Conventional photoplethysmography (PPG) measures time-varying relative changes in the amount of blood in a volume of tissue (typically a fingertip) by detecting changes in the amount of near-infrared light transmitted through the tissue; the greater the amount of blood in the light path, the greater the amount of light absorbed. During intravascular pressure pulse diastole, the aggregate volume in the fingertip blood vessels is smallest, and during systole, the volume is greatest, as illustrated in FIG. 1, which shows a conventional PPG measurement of aggregate fingertip blood volume during a single blood pressure pulse.

By comparison, fluorescence-mediated photoplethysmography (FM-PPG), according to the various aspects of the invention, measures relative timevarying changes in the amount of blood in a volume of tissue (e.g., skin) by detecting changes in the amount of near-infrared fluorescence light emitted from the tissue volume (section). In FM-PPG, according to the various embodiments, fluorescence intensity is directly proportional to the total amount of a fluorescence dye (e.g., indocyanine green (ICG) dye) present in the blood, and thus becomes a measure of blood volume. In various embodiments, implementation of FM-PPG for quantification of absolute tissue perfusion allows determination of molar concentration of fluorescence dye in circulating blood of a subject during acquisition of an image (or a plurality of images) in an angiogram sequence.

According to various embodiments, FM-PPG and certain characteristics of the administered fluorescence dye, such as for example, concentration fluorescence quenching and a linear relationship between concentration and dual-wavelength ratiometric fluorescence measurements, make possible determination of tissue (e.g. skin) blood flow in absolute terms of volume/time/area. In various embodiments, the method and system of the present invention can be applied across a wide size range of tissue (e.g., skin and ocular fundus) areas, ranging in size, for example, from less than about 1 cm$^2$ to about ¼ m$^2$.

In various embodiments, suitable fluorescence dyes include any non-toxic dye which fluoresces when exposed to light energy in an amount sufficient to cause the fluorescence dye to fluoresce thereby permitting the subject tissue area to be imaged. In various embodiments, the dye may be administered at a suitable concentration such that the fluorescence may be detected when the appropriate wavelength of radiant energy is applied. In certain embodiments, the dye is a fluorescent dye that emits light in the infrared spectrum. In certain embodiments, the dye is a tricarbocyanine dye such as indocyanine green (ICG). In other embodiments the dye is selected from fluorescein isothiocyanate, rhodamine, phycoerythrin, phycocyanin, allophycocyanin, o-phthaldehyde, fluorescamine, rose Bengal, trypan blue, fluoro-gold, or a combination thereof. The aforementioned dyes may be mixed or combined in certain embodiments. In some embodiments, dye analogs may be used. A dye analog includes a dye that has been chemically modified, but still retains its ability to fluoresce when exposed to radiant energy of an appropriate wavelength.

In some embodiments, the dye may be administered to a subject (e.g., a mammal) intravenously, e.g., as a bolus injection, in a suitable concentration for imaging. In various embodiments, the dye is injected into a vein or artery. In embodiments where multiple dyes are used, they may be administered simultaneously, e.g. in a single bolus, or sequentially, e.g. in separate boluses. In some embodiments, the dye may be administered by a catheter. In various embodiments, the dye may be provided as a lyophilized powder or solid. In certain embodiments, it may be provided in a vial, e.g. a sterile vial which may permit reconstitution to a suitable concentration with a sterile syringe. It may be reconstituted using any appropriate carrier or diluent. Examples of carriers and diluents are provided below. The dye may be reconstituted, e.g., with water, immediately before administration.

In certain embodiments, the dye may be administered to the subject less than an hour in advance of obtaining an image. In some embodiments, the dye may be administered to the subject less than 30 minutes in advance of obtaining an image. In yet other embodiments, the dye may be administered at least 30 seconds in advance of obtaining an image. In still other embodiments, the dye is administered contemporaneously with obtaining an image.

In various embodiments, any diluent or carrier which will maintain the dye in solution may be used. As an example, in certain embodiments where the dye is ICG, the dye may be reconstituted with water. In other embodiments where the dye is ICG, the dye may be reconstituted with an alcohol, e.g. ethyl alcohol. In some embodiments, once the dye is reconstituted it may be mixed with additional diluents and carriers. In some embodiments, the dye may be conjugated to another molecule, e.g., a protein, a peptide, an amino acid, a synthetic polymer, or a sugar e.g., to enhance solubility or to enhance stability. Additional examples of diluents and carriers which may be used in certain embodiments include glycerin, polyethylene glycol, propylene glycol, polysorbate 80, Tweens, liposomes, amino acids, lecithin, dodecyl sulfate, phospholipids, deoxycholate, soybean oil, vegetable oil, safflower oil, sesame oil, peanut oil, cottonseed oil, sorbitol, acacia, aluminum monostearate, polypxylethylated fatty acids, and mixtures thereof. Additional buffering agents may optionally be added including Tris, HCl, NaOH, phosphate buffer, HEPES.

According to the various embodiments, FM-PPG measures time-varying changes in the amount of blood in a volume (section) of tissue by detecting changes in the amount of near-infrared fluorescence light emitted from the tissue volume, following administration (e.g., intravenous injection) of a fluorescence dye (e.g., ICG) to a subject. Fluorescence intensity is proportional to the total amount of the fluorescence dye (e.g., ICG) contained in the blood.

Figure 2:
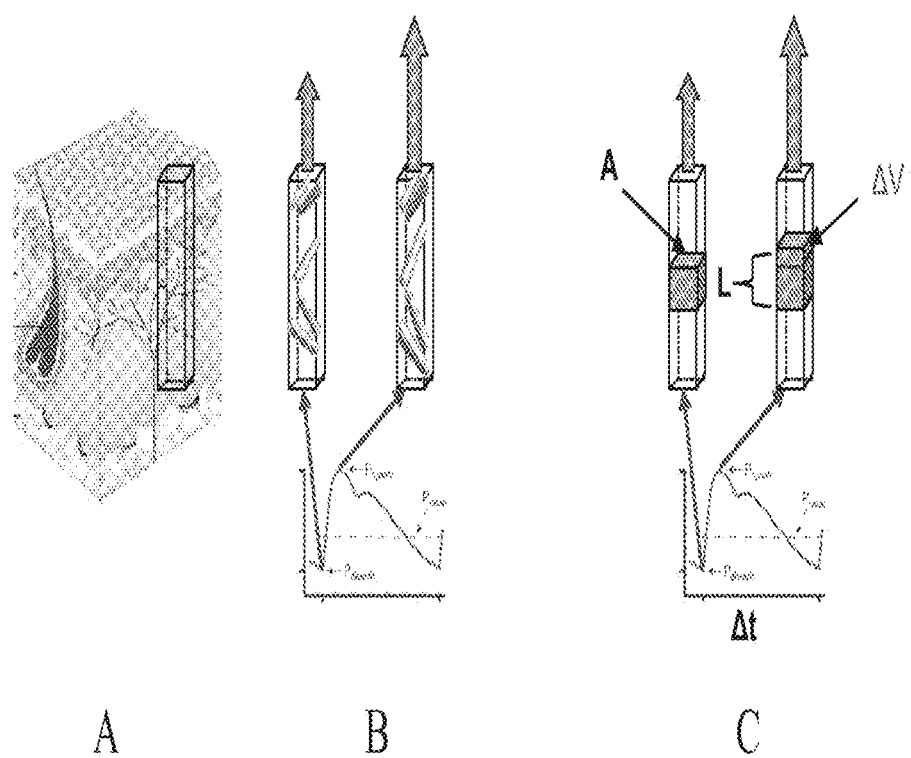
FIG. 2A-2C illustrate the use of fluorescence-mediated photoplethysmography (FM-PPG), according to an embodiment, to measure time-varying changes in blood volume in a volume (section) of tissue having a surface area, A, by detecting changes in fluorescence intensity.

The individual ICG-filled vessel segments within the rectangular volume of skin tissue (a section of tissue) indicated in FIG. 2A are schematically represented in FIG. 2B, wherein the vessel segments are depicted during pressure pulse diastole (on the left) and during the peak of systole (on the right). The arrows on the surfaces of the tissue volumes (each having a cross-sectional area, A) indicate the increase in ICG fluorescence intensity that occurs when the diameters of the individual blood vessel segments increase as blood pressure rises from the diastolic to the systolic level. FIG. 2C replicates the geometrical relationships depicted in FIG. 2B, except that the aggregate volumes of the individual blood vessel segments are represented by a single cubic volume. Additionally, the maximum amount of blood volume increase that occurs between the diastolic and systolic pressures is indicated as ΔV.

The total amount of blood flowing through the rectangular tissue volume during a single pressure pulse oscillation is proportional to the area beneath the pulse curve. If the pressure pulse were a square-wave, then the total volume flowing during a single pulse would be ΔV. However, the pressure pulse curve is not a square-wave, so the area under the actual pulse curve is a fraction of the square-wave area.

Therefore, let pulse duty-cycle ($P_{DC}$) may be defined as the fraction of the area under the square wave occupied by the area under the actual pulse curve. Thus, the actual blood flow through the tissue volume during one pressure pulse cycle, F, is:

$$F=(\Delta V)(P_{DC})/\Delta t,$$

where
ΔV=(cross-sectional area of the tissue volume end, A)× (thickness increase, ΔL, of the blood volume layer, L), and
Δt=duration of a single pressure pulse,
therefore, $$F=(A)(\Delta L)(P_{DC})/\Delta_t \qquad (1)$$

Although absolute values can be determined for A, $P_{DC}$, and Δt, no clinically acceptable method by which to routinely determine ΔL has been demonstrated previously. Exemplary algorithm embodiments by which ΔL can be determined quantitatively in terms of length/time are described below.

In one embodiment, the concentration-dependent fluorescence quenching displayed by a fluorescence dye (e.g. ICG) provides a method by which ΔL can be determined quantitatively in terms of length/time.

Concentration-dependent fluorescence quenching is the phenomenon exhibited by certain dyes in solution, wherein the fluorescence intensity emitted by the solution increases along with dye concentration until a point is reached beyond which further concentration increase results in fluorescence diminution. For example, for ICG in blood, maximum fluorescence occurs at a concentration of 0.025 mg/ml (see Flower, R. W. and Hochheimer, B. F.: "Quantification of Indicator Dye Concentration in Ocular Blood Vessels", Exp. Eye Res., Vol. 25: 103, August 1977); above or below this concentration, fluorescence diminution occurs fairly sharply, as shown in FIG. 3A, which schematically illustrates the time-varying relationship between ICG concentration and fluorescence intensity during transit of ICG through a blood vessel. FIG. 3B schematically illustrates, for a fixed location within a blood vessel, the time-varying relationship between ICG concentration (solid curve) and fluorescence intensity (dashed curve) during transit of an ICG dye bolus through the vessel.

FIG. 3 indicates the points at which dye concentration in both FIG. 3A and FIG. 3B is 0.025 mg/ml, and the points at which the concentration is at some significantly greater level at which fluorescence quenching takes place (e.g., in this example, about 10 times greater). FIG. 3B illustrates that as an ICG bolus transits the blood vessel and dye concentration increases (solid curve), ICG fluorescence also increases (dashed line) and reaches a maximum intensity when the dye concentration reaches 0.025 mg/ml (left-hand arrow). As concentration continues to increase, fluorescence decreases due to concentration fluorescence quenching, reaching a minimum intensity (middle arrow) when concentration reaches its maximum (about 0.250 in this example). Thereafter, concentration decreases, causing fluorescence intensity to increase, until it again reaches the maximum level of 0.025 mg/ml (right-hand arrow); then as concentration continues to decrease, fluorescence also begins to decrease again.

In various embodiments, the distinctive double peaks of equal maximum fluorescence intensity that occur during transit of an ICG bolus of sufficiently high concentration and volume integrity allow to determine, in absolute terms, the increase in blood volume thickness, ΔL, depicted in FIG. 2C. Since the peaks occur at a concentration of 0.025 mg/ml, and since the fluorescence intensity emitted from a known area (A) at the precise time either peak occurs can be determined, the thickness of a layer of blood containing 0.025 mg/ml ICG that emits the same fluorescence intensity under identical conditions of illumination and magnification also can be empirically determined.

For example, using the same optical device and fluorescence excitation illumination used to acquire the high-speed angiographic images from which the intensity of the double-peaked fluorescence was obtained, a fluorescence image can be obtained of a finely tapered capillary tube filled with a 0.025 mg/ml ICG/blood or ICG/ethanol solution, as is illustrated, for example, in FIG. 4. From this image (FIG.

4A), a graph of the linear relationship between capillary diameter, ΔL, and fluorescence intensity can be generated (FIG. 4B).

Absolute values are now known for all the terms in the equation F=(A×ΔL)/Δt, making it possible to solve for absolute blood flow through the volume of skin tissue lying beneath area A in terms of ml/sec. Therefore, this embodiment, illustrates a method for absolute quantification of blood flow in a volume of tissue (e.g., skin blood flow) previously unavailable to clinicians.

Figure 5:
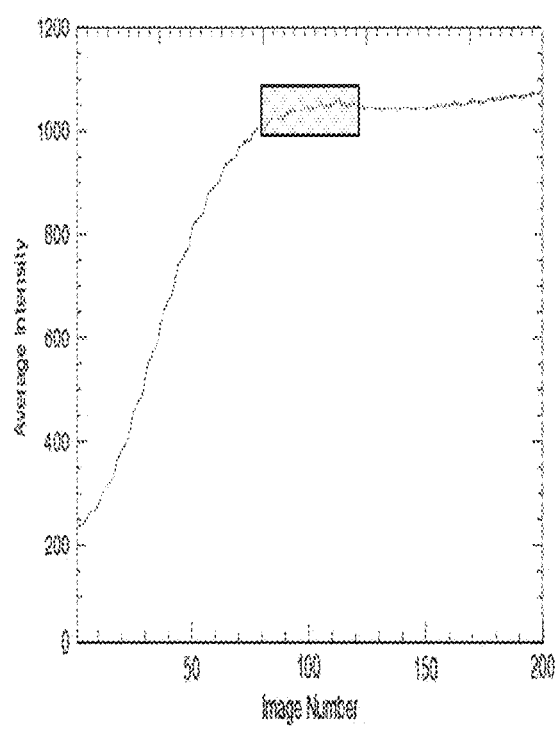
FIG. 5 is a plot of time-varying average fluorescence intensity emitted from an area of human forearm skin following injection of an ICG solution into the cubital vein.

In another embodiment, following rapid cubital vein injection of 0.40 ml of 50 mg/ml aqueous ICG dye and an immediate, rapid 5.0-ml isotonic saline flush, high-spatial resolution angiographic images of a 250 mm² area of human medial contralateral forearm skin were obtained at the rate of 23/sec. The individual images in the angiogram sequence were re-registered to remove frame-to-frame arm movement, and from each of these images, average fluorescence intensity for the tissue area was calculated for each image. These data were then used to generate a plot of time-varying average fluorescence intensity, a portion of which (centered approximately about Image Number 100) is shown in FIG. 5.

Figure 6:
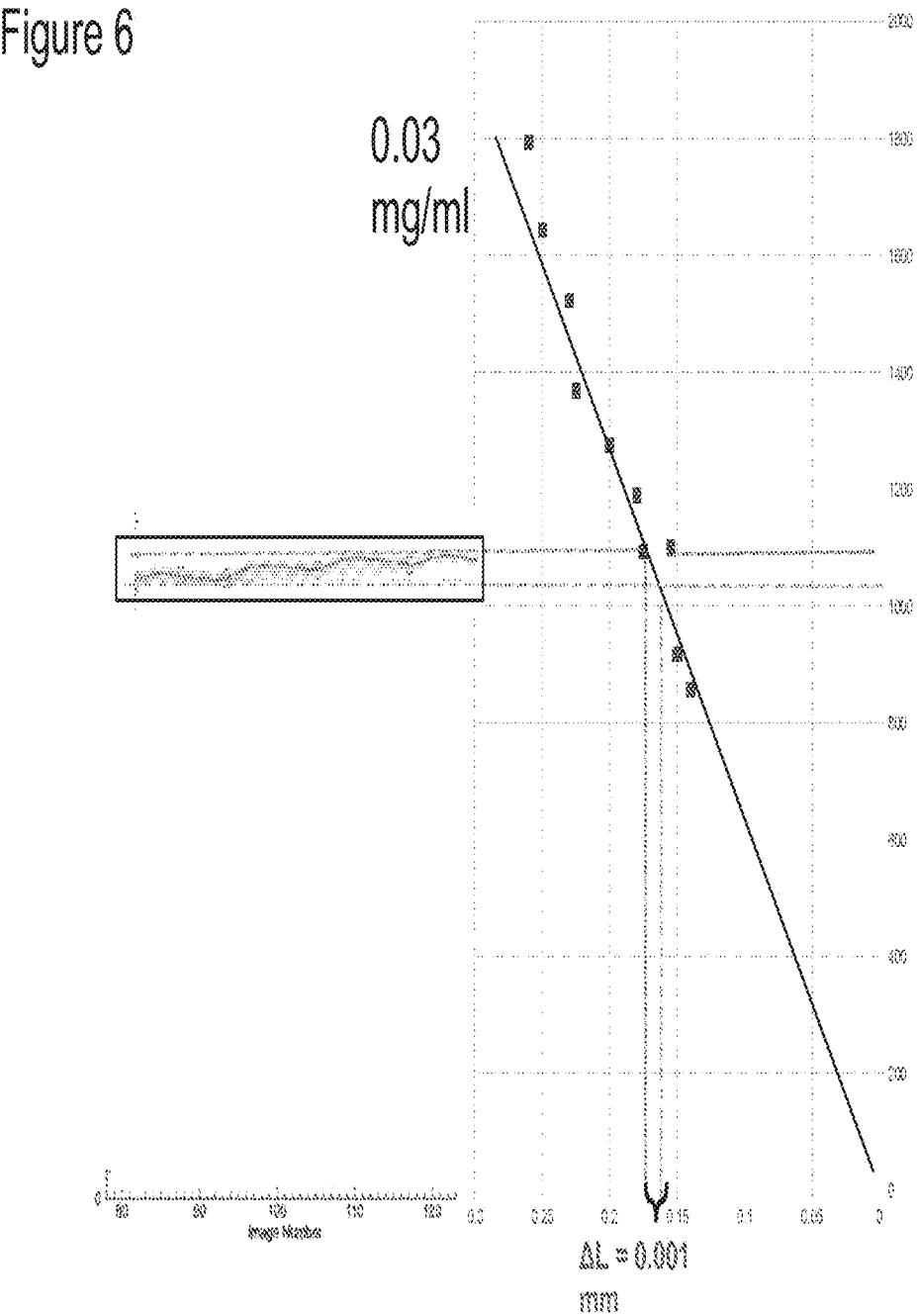
FIG. 6 shows a train of PPG oscillations associated with a plot of fluorescence intensity emitted from a tapered capillary tube containing a 0.03 mg/ml concentration ICG solution as a function of capillary tube thickness.

High-frequency "PPG" oscillations are clearly visible riding on the low-frequency component of the fluorescence intensity curve which is related to dye filling of the aggregate vascular volume contained within the volume of skin tissue, beneath the 250 mm² surface area. As is illustrated in FIG. 6, three PPG oscillations (and a fraction of a fourth) centered about image number 100 have been juxtaposed beside a graph of the capillary diameter versus fluorescence data from FIG. 4B. Both graphs are on the same fluorescence intensity scale shown on the right of the figure.

An envelope defined by the minima (dashed line) and maxima (dashed line) of the PPG fluorescence-intensity oscillations is projected onto the fluorescence-intensity versus capillary-diameter graph and then onto the graph's abscissa. The width of the latter projection indicates the thickness of the blood-volume layer increase, ΔL=0.001 mm.

The average pulse duty-cycle ($P_{DC}$) for the three fluorescence-intensity oscillations in this example was determined to be 40%, and the average duration of one pulse was determined to be Δt=0.680 sec.

$$\text{Since } F = (A)(\Delta L)(P_{DC})/\Delta t \quad (1)$$

$$= (250 \text{ mm}^2)(0.001 \text{ mm})(0.40)/(0.680)$$

$$= 0.147 \text{ mm}^3/\text{sec, or } 0.147 \text{ ml/sec}$$

There appears to be little information available in the prior art regarding absolute blood flow in the arm skin due to the unavailability of a reliable measurement methodology. A very rough approximation can be made using the following average blood circulation and anatomical values:

$$\text{Total cardiac output} = 5 \text{ L/min} = 83.33 \text{ ml/sec}$$

$$\text{Fraction of cardiac output of skin} = 20\% \text{ or } 16.67 \text{ ml/sec}$$

$$\text{Skin area(m}^2) = \{[\text{height(in)} \times \text{weight(lbs)}]/3131\}^{1/2} =$$

$$\{[68 \times 154]/3131\}^{1/2} = 1.83$$

$$= 1.83 \times 10^6 \text{ mm}^2$$

Therefore, $$\text{total blood flow to 1 mm}^2 \text{ of skin} = (16.67 \text{ ml/sec})/(1.83 \times 10^6)$$

$$= 9.11 \times 10^6$$

ml/sec Hence, $$\text{blood flow to 250 mm}^2 \text{ of skin} = 250 \times 9.11 \times 10^6 \text{ ml/sec}$$

$$= 0.0023 \text{ ml/sec}$$

This latter approximation of blood flow to 250 mm² of skin is about 60-times less than the 0.147 ml/sec derived using the fluorescence-mediated PPG method and system of the present invention as illustrated in the example above. However, such a discrepancy in results may be accounted for in view of the inherent assumption that blood flow is uniformly distributed throughout the entire body skin area in the calculation based on circulation/physiologic approximations, and that the capillary-diameter/fluorescence-intensity data in the FM-PPG example were compiled using ICG in ethanol rather than blood and by-eye capillary-diameter measurements were made with a superimposed scale rather than by digital means.

In various embodiments, rapid venous injection of a small-volume, high-concentration dye bolus (e.g., ICG), followed by a saline flush to achieve a circulating peak dye concentration in excess of 38-µM, as required in the preceding calibration method, may be suitable for selected clinical implementations.

In another embodiment of the present invention, an alternative calibration method was developed to accommodate the range of peak dye (e.g. ICG) concentrations encountered in routine clinical use.

For example, typical ICG administration consists of injecting about 3 ml of 25 mg/ml aqueous solution, followed by a 5 ml saline flush. Injected dye bolus dilution from about 400 to 600 times occurs during intravascular transit to various sites of interest, resulting in a range of peak dye concentration of approximately 5.4- to 8-µM. To accommodate this variability of peak dye concentrations, additional fluorescence wavelength data is ac qui red simultaneously with the angiographic images; these data are used for dual-wavelength ratiometric analysis for determining intravascular dye concentration at the time each image is acquired.

Whereas the calibration method described in the previous embodiment has the advantage of requiring no other data except an ICG fluorescence angiography sequence, the alternative calibration method described in this embodiment has the advantage of being entirely transparent to the user, in that no deviation from the usual injection technique is required. However, in connection with this embodiment, the recording device's imaging optics is modified to permit continuous simultaneous measurement of two near IR wavelengths longer than those used for image formation.

As with the calibration method described in the previous embodiment, in the alternative calibration method, the thickness increase is determined, ΔL, of the blood volume layer, L, depicted in FIG. 2C, Again, the data to do this are embedded in the fluorescence generated by illumination of the aggregate ICG-dye tagged blood volume in the rectangular tissue volume during a single pressure pulse oscillation. When the surface area, A, of the rectangular tissue volume is illuminated with 805-nm wavelength laser light, the total fluorescence generated, F, is a function of excitation light intensity, i.e., the ICG molar absorption coefficient at 805-nm, £, the ICG molar concentration, C, the ICG quantum efficiency, Φ, and the aggregated ICG-tagged blood layer thickness, L. That is:

$$F=f(Ie,\varepsilon,C,\Phi,L) \quad (2)$$

However, taking into account that the excitation light is absorbed as it travels through ICG tagged blood volume, as described by the Beer-Lambert law of absorption, the intensity of emitted fluorescence light, If, is:

$$If=Ie\Phi(1-e^{-\varepsilon CL}) \quad (3)$$

Solving equation (3) for L:

$$L=\ln [I_e\Phi/(I_e\Phi-I_f)](\varepsilon C)^{-1} \quad (4),$$

wherein values for all the parameters are known, except for the instantaneous ICG molar concentration, C.

Figure 7:
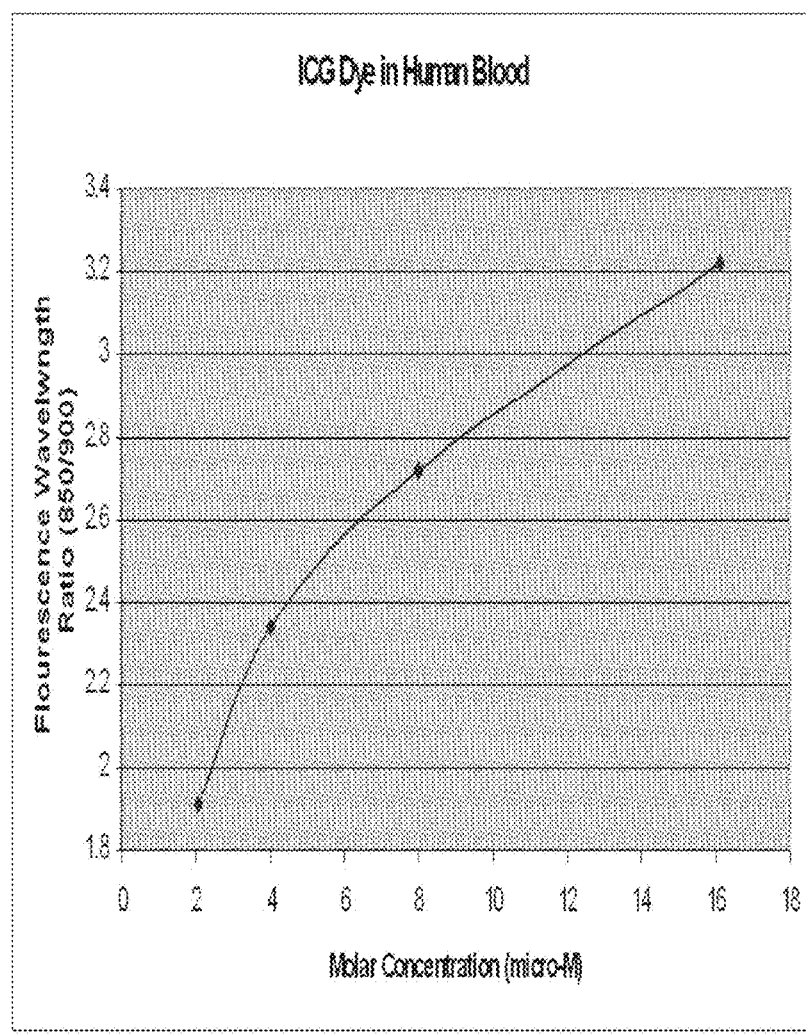
FIG. 7 illustrates the relationship of the ratio of the intensities of bands of wavelengths centered about 850 nm and 900 nm emitted by ICG in blood as a function of molar concentration.

In various embodiments, dye (e.g. ICG) molar concentration, however, can be determined by ratiometric analysis of two appropriate near-IR wavelengths above the band of wavelengths used to form the dye (e.g. ICG) fluorescence images. For example, FIG. 7, below, shows the relationship of the ratio of the intensities of bands of wavelengths centered about 850- and 900-nm wavelengths emitted by ICG in blood as a function of the dye molar concentration. (Note that the range of molar concentrations encompasses, by wide margin, the 5.4- to 8-µM range produced by the current conventional ICG dye administration regimen employed by plastic and reconstruction surgeons. However, the range for which such a relationship extends much farther to both higher and lower molar concentrations.)

Figure 8:
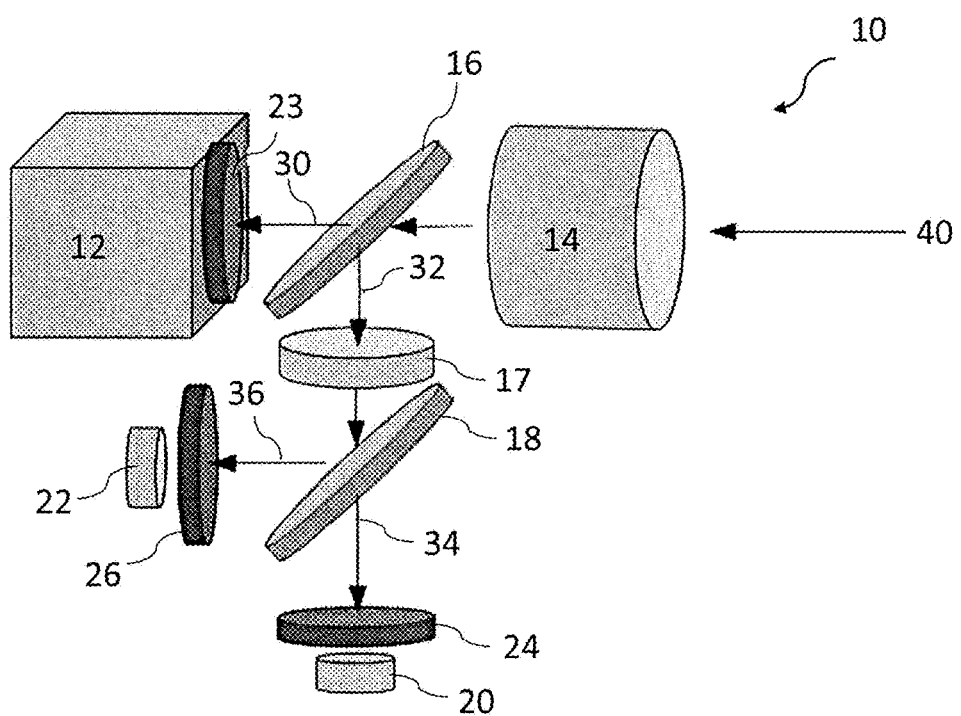
FIG. 8 shows an exemplary imaging system comprising an arrangement of optical components according to an embodiment for implementing the FM-PPG methodology of the present invention.

In various embodiments, implementation of ratiometric dye (e.g. ICG) molar concentration determination involves the addition of optical and electronic components into the fluorescence imaging pathway. An example of the insertion of these components, according to an embodiment, is shown schematically in FIG. 8 in the context of the SPY® imaging system by Novadaq Technologies Inc. of Mississauga, Canada. FIG. 8 shows schematically an imaging system 10 which comprises a CCD video camera 12 and objective lens 14 for fluorescence imaging of fluorescence light from tissue 40. As is shown in the embodiment in FIG. 8, the addition of optical and electronic components (e.g., component 16) into the fluorescence imaging pathway may comprise disposing such components between the SPY® objective lens 14 and the CCD video camera 12. Signal outputs from the two Si photo-detectors 20 an d 22 shown in FIG. 8 are real-time analyzed utilizing the relationship in FIG. 7, and the resultant molar concentration determined for each angiographic image will be embedded in its TIFF header and subsequently extracted as needed to determine the instantaneous dye molar concentration in the circulating blood. The embodiment in FIG. 8 is discussed in more detail below in connection with the example of hardware implementation.

In various embodiments, the increase in thickness of the blood volume layer, ΔL, that occurs during a pressure pulse can be determined at any time during the angiographic sequence by using equation (4) to determine the layer thickness at the peak of a pressure pulse, $L_p$, and at the pulse minimum, $L_m$, and then calculating the difference between the two:

$$\Delta L=L_p-L_m=\ln [(I_e\Phi-I_m)/(I_e\Phi-I_p)](\varepsilon C)^{-1} \quad (5),$$

where $I_p$ and $I_m$ are the respective fluorescence intensities measured at the pulse peak and minimum, and where $$L=\ln [Ie\Phi/(Ie\Phi-If)](\varepsilon C)^{-1},$$

wherein,
L=aggregate thickness of blood layer in all vessels beneath area A
(cm) Ie=excitation light intensity (W cm$^{-2}$)
If=intensity of emitted fluorescence light (W cm$^{-2}$)
ε=ICG molar absorption coefficient (M$^{-1}$ cm$^{-1}$)
Φ=ICG quantum efficiency
(0.13)
A=area of interest (cm$^2$)
C=ICG molar concentration (M)
L is determined at the systolic peak of the blood flow pulse ($L_S$) and at its diastolic minimum ($L_D$), and then flow through the tissue area of interest (A) is calculated as:
Flow=A ($L_S$–$L_D$)/time, and wherein, time is reckoned as the duration of the blood flow pulse.

In various embodiments, the fluorescence intensities $I_p$ and $I_m$ may be determined, for example, using the same data used in the example algorithm depicted in FIG. 6, wherein the average intensity levels forming an envelope about the pressure pulses from the angiogram images are represented by the dashed horizontal lines. In the present example, however, those two horizontal are projected to the relative fluorescence intensity scale on the right-hand side of the graph; one line intercepts the ordinate at 1100, and the other line intercepts at 1035.

In various embodiments, in order to convert these relative intensity levels for $I_p$ and $I_m$ to actual light intensity levels (µW/cm$^2$), the CCD video camera was used as a light meter by calibrating the camera's gray scale output against controlled dye (e.g., ICG) fluorescence intensity input levels.

The calibration method was devised to take into account that the total fluorescence ($I_f$, equation 3) is emitted spherically, and that only a fraction of it is detected by the camera, dependent upon the aperture diameter of the imaging system and the distance of the aperture from the emitting source. The camera's output was found to be linear from approximately 50- to 2500-µW, such that:

$$I_f(\mu W) = (\text{avg. intensity} - 100)/413.012 \quad (6)$$

therefore, $$I_p = 2.905 \text{ µW},$$

and $$I_m = 2.749 \text{ µW}.$$

Noting that during acquisition of the angiogram data depicted in FIG. 6, $$I_e = 4.0 \text{ W},$$

equation (5) becomes:

$$\Delta L = \ln[((4000 \times 10^3 \times 0.13) - (2.749 \times 10^3))/$$
$$((4000 \times 10^3 \times 0.13) - (2.905 \times 10 - 3))](\varepsilon\ C)^{-1}$$
$$= 0.0005 \text{ mm}$$

Inserting this value for ΔL into equation (1):

$$F = (A)(\Delta L)(P_{DC})/\Delta t$$
$$= (250 \text{ mm}^2)(0.0005 \text{ mm})(0.40)/(0.680)$$
$$= 0.0735 \text{ mm}^3/\text{sec, or } 0.0735 \text{ ml/sec},$$

This blood flow (0.0735 ml/sec) is half that calculated by the previous method (0.147 ml/sec) used in the first example, making it closer to the approximation of 0.0023 ml/sec that was based on whole-body physiological parameters.

Variations in skin blood flow are induced by changes in a number of physiological parameters, as well as by changes in ambient temperature. To determine the magnitude of such variations, an experiment was performed in which two ICG angiograms of the same 250 mm$^2$ area of human forearm skin as in the example above were recorded within a period of 32 minutes, each following rapid injection of 0.33 ml of 25 mg/ml ICG and a 5 ml saline flush into the contralateral cubicle vein. The first angiogram was recorded at an ambient room temperature of about 70° F., and the second was recorded immediately after exposure for about 1 minute to radiation from a 24 W quartz halogen lamp at a distance of 6 inches; the temperature sensation was similar to that produced by rapid exhalation of breath through the mouth at a distance of several inches.

Figure 9:
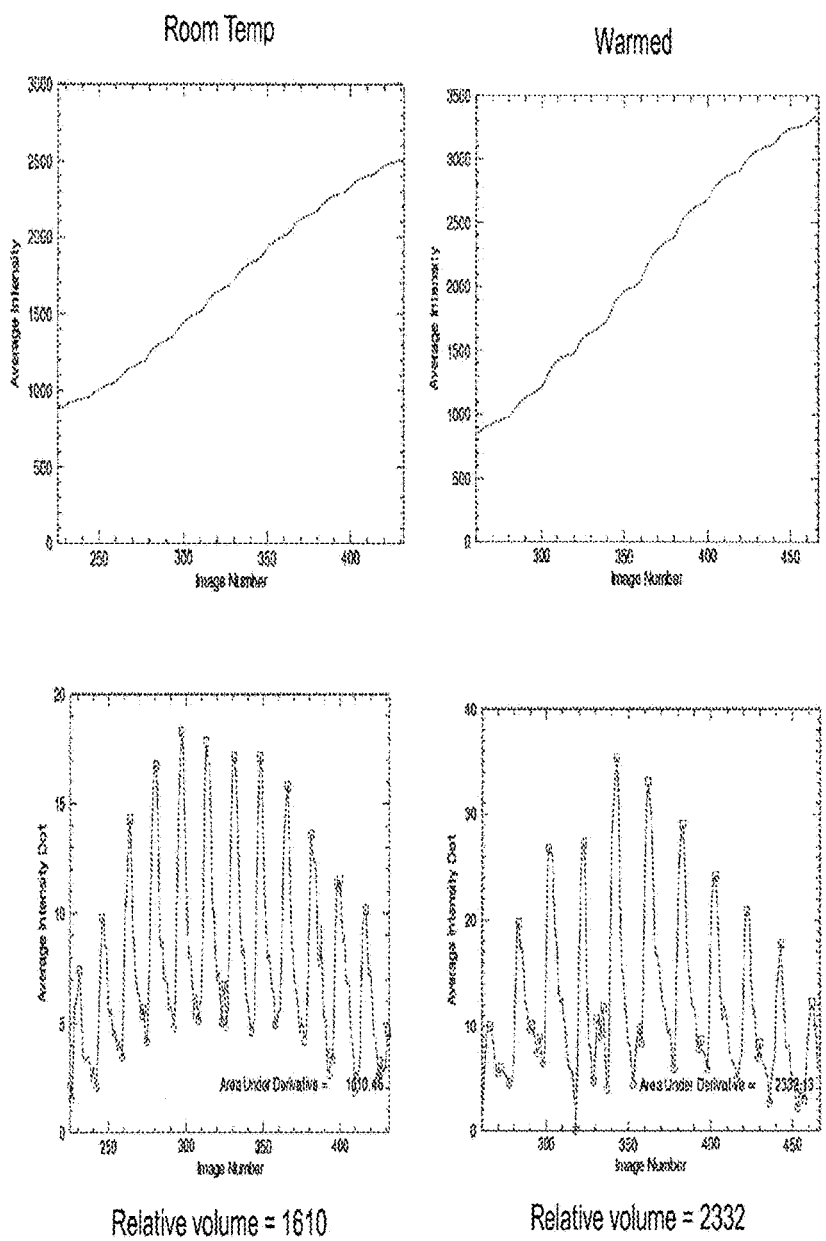
FIG. 9 displays segments of time-varying average intensity graphs from certain working examples of the present invention contained herein.

FIG. 9 shows segments of the time-varying average intensity graphs from the two experiments (top row) along with their respective first-derivative with respect to time graphs (bottom row). Since this experiment was performed prior to implementation of the calibration part of the FM-PPG algorithm, the calculated skin area blood flows at the bottom of the figure are only in relative terms, rather than the absolute terms of ml/sec. Nevertheless, the fact that blood flow was about 1.4 times greater at slightly elevated temperature, compared to ambient room temperature, is an indication of the range of variability in normal skin tissue that might be expected in FM-PPG blood flow measurements unless temperature and other physiological parameters at the time of data collection are not taken into account.

According to an embodiment of the FM-PPG method and system of the present invention, ICG was administered intravenously to a subject by injecting an ICG dye bolus of sufficiently high concentration that, during transit through the tissue site of interest, peak dye concentration would exceed 0.025 mg/ml (the maximum fluorescence intensity, and where concentration fluorescence quenching starts as described in more detail below). Under those conditions, the sub-sequence of angiogram images recording dye transit contained the information needed to determine ICG molar concentration for each image in the entire sequence as a function of image gray-scale intensity, assuming dye excitation level was constant throughout angiogram recording and that fluorescence-intensity vs. CCD camera gray-scale-output is known.

In various embodiments, to counteract ICG dye fluorescence quenching, a real-time, two-wavelength ratiometric method for determination of ICG molar concentration in circulating blood was developed. It involves no special preparation, no deviation from a practitioner's usual regimen for dye injection, nor that the transit-phase of dye through the tissue of interest necessarily be recorded, but that fluorescence excitation intensity be maintained at a known constant level during image acquisition and that angiography not be performed when circulating blood is dye-saturated or that significant vascular staining has occurred. In various embodiments, implementation of the wavelength-ratiometric method involves additional optics and hardware and software for determining, simultaneously with each image acquired, the intensities of two bands of near-IR-wavelengths and for embedding these data in the corresponding image header. So far as angiogram acquisition is concerned, these additions and events are entirely transparent to the operator of any device incorporating them.

In various embodiments, additional calibration steps are carried out on each device prior to its entering routine clinical use.

An Example of Hardware Implementation

According to an embodiment, for evaluation of the ratiometric method of ICG molar concentration, the ICG fluorescence imaging optical path of a prototype FM-PPG system such as, for example, the imaging system 10 shown in FIG. 8, was modified by insertion of a beam-splitter 16 between the objective lens 14 and CCD video camera 12 as is illustrated in FIG. 8. In this embodiment, the beam splitter 16 transmitted the band of ICG fluorescence wavelength(s) 30 used for image capture (approximately 815 to 845 nm wavelengths, which may be filtered by a bandpass filter 23) and diverted all higher wavelength(s) 32 (e.g., wavelengths >845 nm) to a parallel path (which may include a relay lens 17), along which the light was further divided by a second beam-splitter 18 into wavelengths less than approximately 875 nm (wavelength(s) 34) and wavelengths greater than approximately 875 nm (wavelength(s) 36). At the ends of these latter pathways were placed near-IR sensitive Si detectors (e.g., Si detectors 20 and 22) (Thorlabs, model PDA36A Si Switchable Gain Detector). Initially, narrow band-width filters centered about 850 (filter 24) and 900 nm (filter 26), respectively, were inserted in front of each of the detectors 20 and 22 to approximate the front-face-excitation fluorescence emission spectral data from whole blood samples containing 2-, 4-, 8-, 16-, and 32-µM ICG (produced under contract by the Berezen Lab at Washington University, St. Louis) used to determine the two wavelengths on which the ratiometric method was based. A subsequent analysis indicated that in another variation, substantially the same ratiometric discrimination could be made using much wider bandwidths. Accordingly, in this embodiment, the narrow band-width filters were removed, thereby increasing the light intensity impinging on the Si detectors. It is noteworthy that the light impinging on each Si detector is reckoned to arise from the entire field of view recorded in each angiogram image. However, due to analysis equipment availability limitations, the post-secondary-beam-splitter light paths and focusing of light onto the Si detectors has not been rigorously verified.

An Example of Software Implementation

Data Acquisition

In this embodiment, each Si-detector amplifier output was connected to one of two input channels of a high-resolution digitizer (Advantech 10M, 12 bit, 4ch Simultaneous Analog Input Card, Model PCI-1714UL-BE), and the trigger output from the CCD video camera was connected to the digitizer's trigger input channel. Digitized outputs from each channel were inserted by the λ-link software into the header of each angiogram image recorded. The digitizer continuously acquired an aggregate of 500 k data samples per second, derived cyclically in equal portions from each of the three input channels. When λ-link detected a rise above the 1.5-volt threshold in the camera trigger channel (signifying onset of a 5-msec pulse of excitation light from the 805-nm laser), data sample counting and recording from the other two channels started. The first 300 samples from the 850-nm channel were excluded (to avoid artifact associated with laser pulse rise time), the next 600 samples were recorded (empirically determined to be the optimal amount), and rest were excluded; the same acquisition algorithm was then applied to samples from the 900-nm channel. When the trigger channel voltage dropped below 1.5 volts at the end of the laser pulse, the program was primed to look for the next voltage rise above the threshold level.

Data Analysis

The analysis part of the λ-link software was constructed that in the Phi-motion mode, intensity data from the 850- and 900-nm wavelength bands of light simultaneously embedded in each recorded angiogram image were extracted, producing two streams of digital voltage from the Si detector amplifiers. Each stream contained 600 data samples per excitation laser pulse (i.e., per image), so a total of 1,200 data samples were stored in each image header.

The average level of the voltage samples from the 850-nm channel was divided by the average level of the samples from the 900-nm channel, producing a ratio that is transformed (via the calibration curve) into a μM-concentration of ICG (C) used to calculate absolute tissue perfusion.

The digitized outputs from the two channels, as well as the 2-wavelength ratio, were reported to 6 decimal places. It was empirically determined that the rolling average ratio from 40 consecutive images (the number recorded in approximately 1.7 seconds) was stable to 3 decimal places, therefore the last three are truncated for purposes of calculation and reporting.

Construction of the 2-wavelength Ratio vs C Calibration Curve

The calibration curve associated with the example prototype system is unique to the particular combination of parameters related to both its electrical and optical components (e.g., lens aperture, excitation laser power, Si-detector amplification, etc.), many of which have been optimized by empirical experimentation. Necessary characteristics of the curve are that it is monotonic, has a slope (positive or negative) sufficiently steep to permit adequate resolution for determining ICG concentration in blood, is reproducible for the given fixed set of device parameters, and that it is essentially independent of sample thickness.

Experimental Setup and Data Acquisition

Construction of the calibration curve for the prototype system was based on samples of freshly acquired, anticoagulated whole human blood containing 2-, 4-, 8-, 12-, and 16-μM concentrations of freshly reconstituted ICG dye. Three milliliters of each sample was placed in an open-top Petri dish, producing a 1.764-mm thick layer of blood with a large enough surface area to completely fill the device's field of view.

One by one, each of the five samples was positioned under the objective lens 14 of the imaging system 10, and a sequence of angiographic images approximately 5-sec long was recorded; this procedure was repeated twice more, as quickly as possible to avoid settling of the erythrocytes suspended in plasma. One-half milliliter of blood was removed from each sample, reducing the blood layer thickness by 0.294 mm, and again three sets of angiographic sequences of the five samples were recorded. Then an additional 0.5 ml of blood was removed from each sample, and the final three sets of angiographic sequences were recorded. Thus, nine sets of ratiometric data were acquired from each of the five ICG/blood samples, three sets each from three different sample thicknesses.

For purposes of comparison, identical sequences of ratiometric data were acquired from five samples of ICG in ethanol having a range of ICG concentrations identical to that of the ICG/blood samples. In this case, however, only one angiographic sequence instead of three was recorded from each of the five samples per sample layer thickness. This deviation from the ICG/blood protocol was necessitated by the fact that absorption of excitation light energy, especially with the higher ICG concentration samples, accelerated ethanol evaporation, thereby reducing sample layer thickness, as well as increasing sample concentration.

Figure 10:
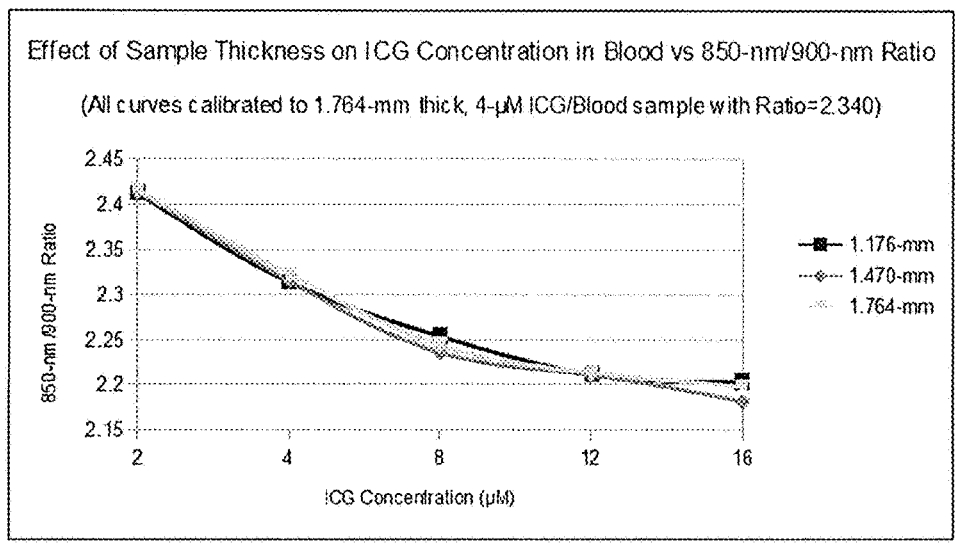
FIG. 10 illustrates the effect of sample thickness on the 2-wavelength ratiometric calibration curves constructed for ICG in ethanol.
Figure 11:
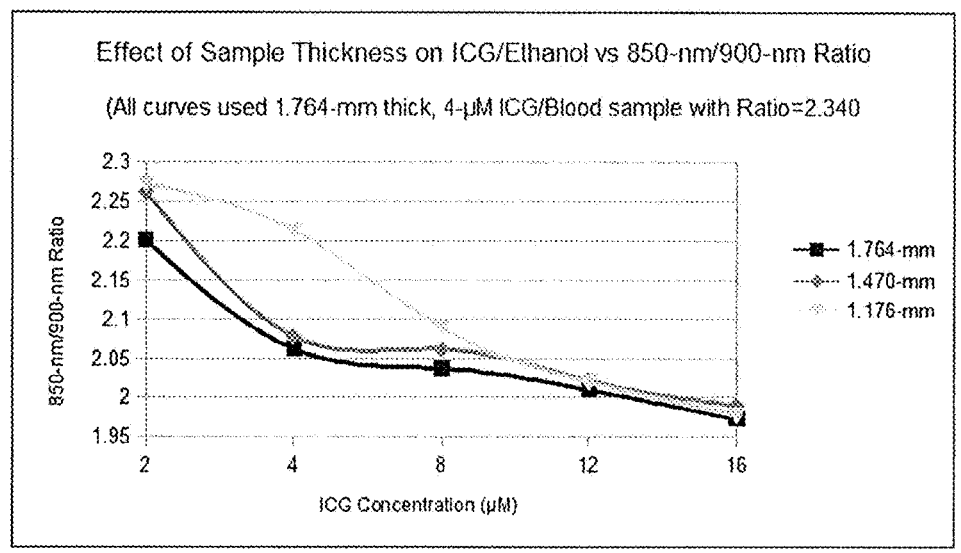
FIG. 11 illustrates the effect of sample thickness on the 2-wavelength ratiometric calibration curves constructed for ICG in human blood.

FIGS. 10 and 11 illustrate the effect of sample thickness on the 2-wavelength ratiometric calibration curves constructed for ICG in ethanol and in human blood, respectively. Although solutions of ICG in whole blood, serum, and ethanol exhibit similar behavior in terms of emitted fluorescence intensity as a function of ICG concentration, the curves in FIGS. 10 and 11 illustrate significantly different behavior between blood and ethanol solutions, especially at lower dye concentrations, in terms of the relationships between intensities of the bands of emitted wavelengths used to construct the 2-wavelength ratiometric calibration curves. A breakdown of the Beer-Lambert law related to differences in chemical interactions (e.g., dissociation and interaction) between ICG and the two solutes may account for this difference. The empirically derived calibration curve for ICG in blood meets the currently understood requisite characteristics as described above in this specification.

Figure 12:
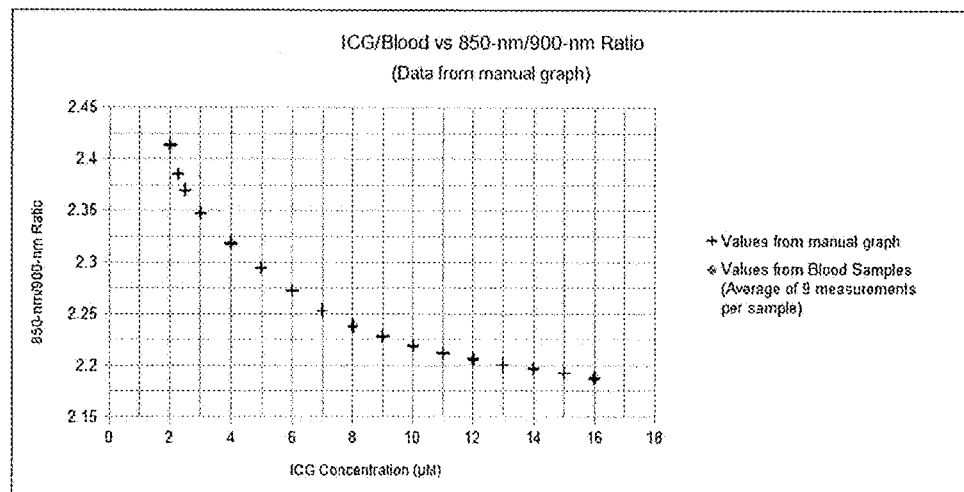
FIG. 12 illustrates a calibration curve interpolated from five data points.
Figure 13:
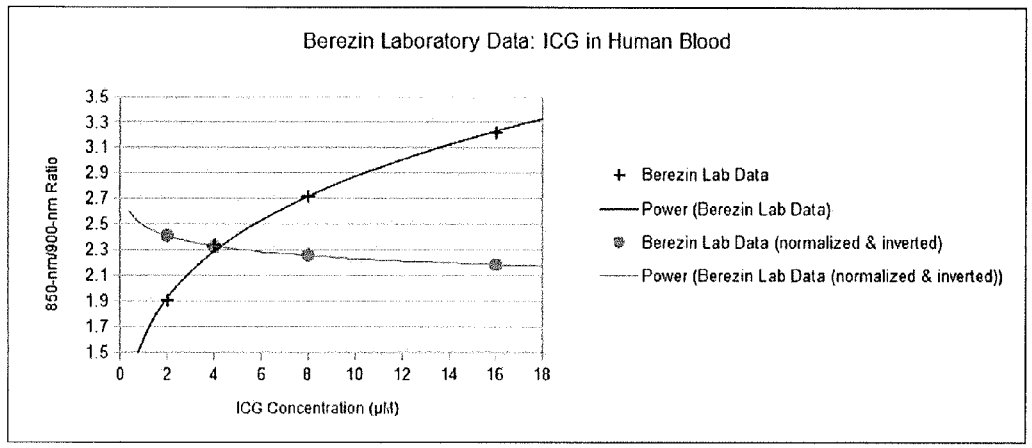
FIG. 13 illustrates Berezin laboratory data for ICG in human blood.

To use the calibration curve in conjunction with the software-embedded algorithm that calculates tissue perfusion, it has to be accessible in a digital format and appear to the software as a continuous function, even though, in this example, it is constructed from only five data points. This may be accomplished by finding an equation describing a smooth curve that passes through all five points. Unfortunately, no linear or second-order polynomial was found that fit satisfactorily, so a graph was manually constructed that does pass through all five points; and from it, twelve additional data points were derived, resulting in the curve in FIG. 12. The software program interpolates between the total of 17 data points. The calibration curve is shown in FIG. 12. As is shown in FIG. 13, average variability of the ratio data along the curve averages +/−0.014.

Comparison of the Current Calibration Data to that from the Berezin Lab

Generation of the fluorescence data from human blood containing various concentrations of ICG used to determine the optimal wavelengths for construction of the ratiometric calibration curve was commissioned to the Berezin Laboratory at Washington University School of Medicine (St. Louis, Mo.). Berezin Lab was one of a few facilities with an available spectrofluorometer having a spectral range far enough into the near-IR region to produce high-resolution data needed to confirm the original data, upon which the 2-wavelength ratiometric method and system were based.

It is expected that the two calibration curves will be different in terms of noise level and resolution, because the Berezin device effectively has a single optical pathway (channel) and uses the same detector to acquire all wavelength data, whereas the prototype system has two separate pathways and uses two different detectors, as well as two different signal amplifiers, etc. Both devises are capable of producing calibration curves that meet the minimum necessary characteristics as described above in this specification, even if the curves look different.

Figure 14:
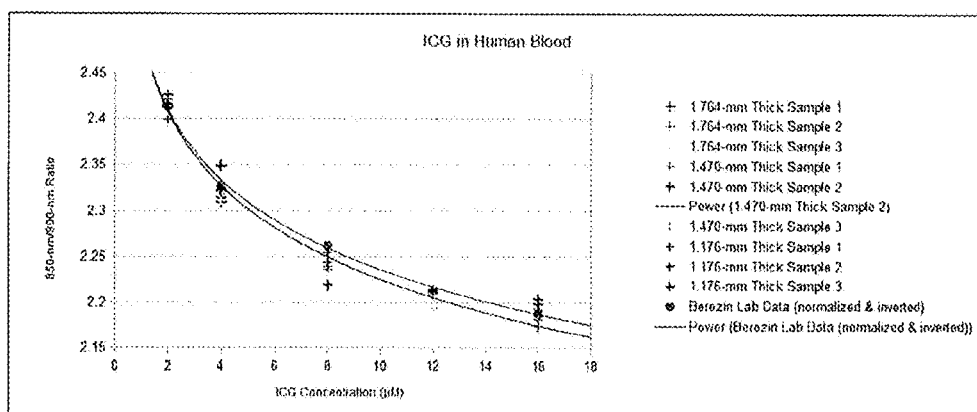
FIG. 14 shows a comparison of the data generated using the FM-PPG exemplary method and system of the present invention (from FIG. 12) with the Berezin laboratory data for ICG in human blood (from FIG. 13)

As comparison of the curve in FIG. 12 and the curve in FIG. 13 (with crosses as data points) demonstrate, they are quite different: although both are monotonic, their slopes are opposite, and the ratio range of the Berezin data is about five times greater. But neither of these invalidates the curve from the prototype system. In fact, by normalizing the ratio scale of the Berezin curve to that of the prototype system (which offsets differences associated with signal intensity and amplification) and by changing the direction of the Berezin data ratio scale (flipping the curve, thereby changing its slope), the resulting curve in FIG. 14 (with circles as data points) closely matches that of the prototype system, as illustrated in FIG. 14.

The transform function used to normalize the Berezin data ratio scale was as follows:

$$R_1 = (R_0/5.796) + 1.858$$

where:

$R_0$ is the original data point value on the Berezin Ratio scale;
$R_1$ is the transformed point value to be plotted on the prototype device Ratio scale;
5.796 is how much larger the Berezin Ratio data range (difference between the 2- and 16-µM Ratio values) and that for the prototype device; and
1.858 is the amount by which $R_1$ for the 16-µM Berezin sample was shifted on the prototype device's scale (after the Berezin curve was flipped) in order to make it correspond to the location of the prototype device's 2-µM data point.

The computer-generated second-order polynomial curve (labeled "Power") for the prototype system data does not fit well; this is underscored by the skewness with which it pass through the spread of "+" data points for both the 8- or 16-µM concentrations.

Nevertheless, significantly the transformed and flipped "Power" curve for the Berezin data lies entirely within the average-variability envelope of the prototype device's "Power" curve, as delineated by the spreads of data points. This demonstrates that the absolute values of the inter-point relationships for both the Berezin and prototype device data are essentially the same. Therefore, by the best measure currently available, the hard- and soft-ware for determination of ICG concentration in blood appear to be optimized and adequate for human subject evaluation.

Validation of the Absolute Tissue Perfusion Algorithm

Due to a dearth of published data regarding absolute blood flow levels through various tissues, validation of the tissue perfusion analysis program is difficult beyond rudimentary bench-top experiments. There being no available data regarding readily accessible tissue for comparison, proof-of-concept of the algorithm and prototype device in living tissue heretofore has been in connection with analysis of angiogram data acquired from the medial forearm.

The only blood flow data rendered in absolute terms from tissue accessible without invasive procedures that might serve as a gold standard for comparison was derived from rhesus monkey ocular tissues by Alm and Bill (Exp. Eye Res. 15: 15-29, 1973). These data were derived from, using the well-established method of radiolabeled microsphere injection, are rendered in terms of mg/min/mm$^2$. Conversion of their data to µL/sec/mm$^2$ requires knowing only that the average density of blood is 1.06×10$^3$ kg/m$^3$, the following relationship is easily derived:

$$X(mg/min/mm^2)/63.6 = X(\mu L/sec/mm^2)$$

According to an embodiment, for acquisition of angiographic data from ocular tissue; a fundus camera may be used. However, a fundus camera has no provision for simultaneous acquisition of the additional two wavelengths of data needed for ratiometric determination of the concentration of ICG in circulating blood (C). However, there are alternative ways to determine when during the transit of an ICG bolus, a concentration of 32.2 µM was reached, and a short sequence of images recorded at that time could be analyzed by the FM-PPG algorithm, the results of which can be compared to that of Alm and Bill.

One alternative method is based on concentration fluorescence quenching, a phenomenon exhibited by ICG dye in solution, wherein the fluorescence intensity emitted by the solution increases along with dye concentration until a point is reached beyond which further concentration increase results in fluorescence diminution. For ICG in blood, maximum fluorescence occurs at a concentration of 0.025 mg/ml; above or below this concentration, fluorescence diminution occurs fairly sharply. As an injected ICG bolus transits a network of blood vessels and dye concentration increases, ICG fluorescence also increases and reaches a maximum intensity when the dye concentration reaches 0.025 mg/ml. As concentration continues to increase, fluorescence decreases due to concentration fluorescence quenching, reaching a minimum intensity when concentration reaches its maximum. Thereafter, concentration decreases, causing fluorescence intensity to increase, until it again reaches the maximum level of 0.025 mg/ml; then as concentration continues to decrease, fluorescence also begins to decrease again. Thus, in a plot of overall image brightness versus image number for a sequence of ICG fundus angiograms in which quenching occurred would contain distinctive double peaks of equal fluorescence intensity. Such quenching can be induced in the ocular vasculatures by injecting an ICG bolus of sufficiently high concentration and volume integrity, but only if the dye injection and an immediately following saline flush of proper volume are made rapidly.

A second alternative is based on previously determined amounts of dilution that cubital vein injected dye boluses undergo during transit to the ocular blood vessels (Invest. Ophthal. 12:881-895, 1973): 310 times in an average adult rhesus monkey, and 600 times in an average adult human. Again, a plot of overall image brightness versus image number for a sequence of ICG fundus angiograms can be used, this time simply to determine the subset of angiogram images that were acquired during peak brightness. The peak brightness is then associated with an ICG concentration 1/600 (in human) or 1/310 (in rhesus) that of the injected dye bolus concentration.

Validation Data from a Rhesus Monkey Eye

In this example, the subject is the dilated right eye of an anesthetized 8.79-kg rhesus monkey (nearly identical to cynomolgus monkeys). Three angiographic sequences were recorded, as follows:

Sequence 1—saphenous vein injection of 0.1 ml (25 mg/0.7 ml ICG solution) followed immediately by a rapid 3.0 ml saline flush.

Sequence 2—3.0 minutes later with no additional dye injection

Sequence 3—3.0 minutes later, saphenous vein injection of 0.1 ml (25 mg/0.5 ml ICG solution) followed immediately by a rapid 3.0 ml saline flush.

Figure 15:
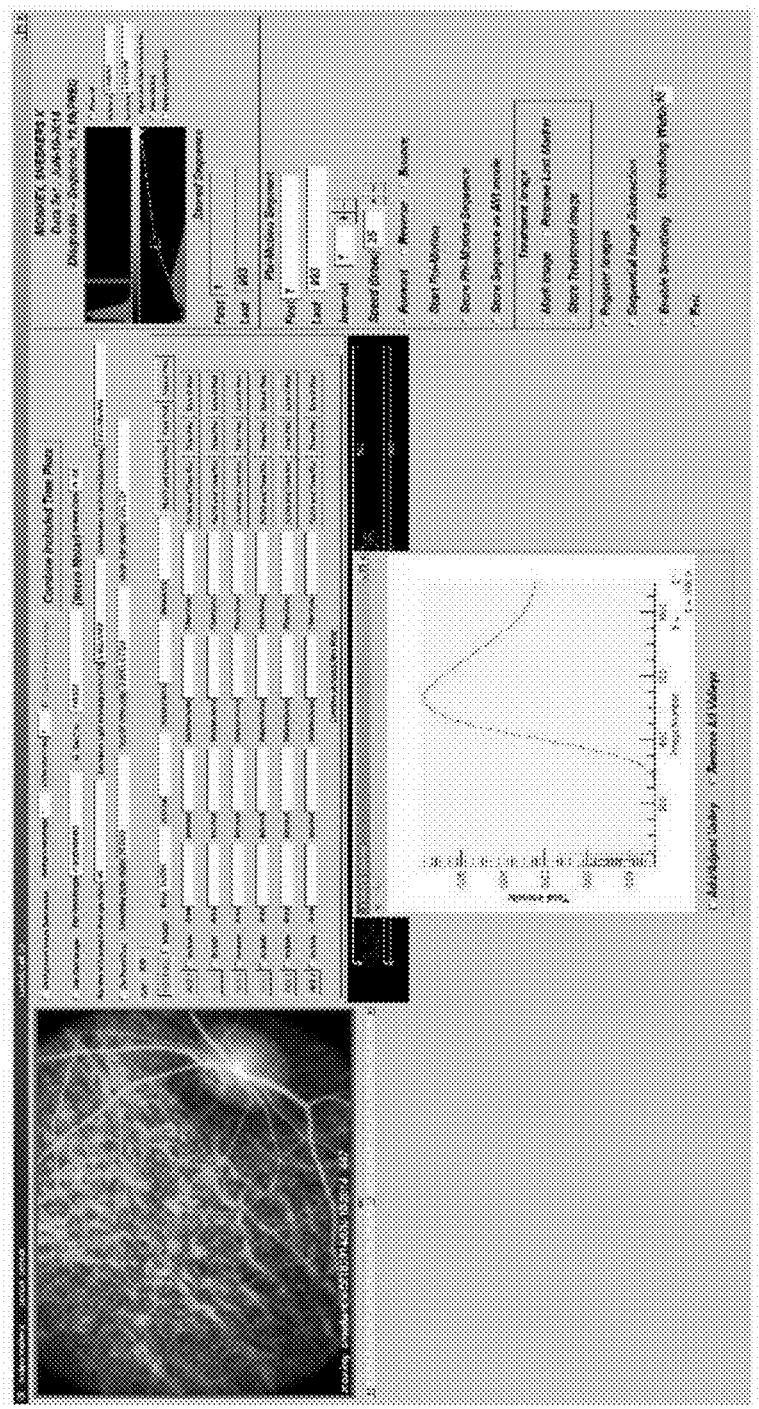
FIG. 15 shows validation data from a Rhesus monkey eye, and in particular, for analysis of each sequence a time plot of image brightness (total intensity) vs, image number.

For analysis of each sequence, a Time Plot of image brightness (Total Intensity) versus image number was constructed for the first sequence, as shown in FIG. 15. From that plot, it was determined the subsequence of images 490-565 were at peak brightness. Since no double peak was detected, the second alternative method for determining the concentration of ICG in circulating blood, as previously described above, was used. That is, the concentration of the first ICG bolus injected was 25 mg/0.7 ml=35.7 mg/ml, which was diluted by 310 times, to a concentration of 0.115 mg/ml during its transit to the eye. Therefore, the peak concentration of dye in the ocular vessels (corresponding to images 490-565) was 148 µM; that value was entered into the appropriate box on the analysis window in lieu of having 2-wavelength ratiometric data available.

Figure 16:
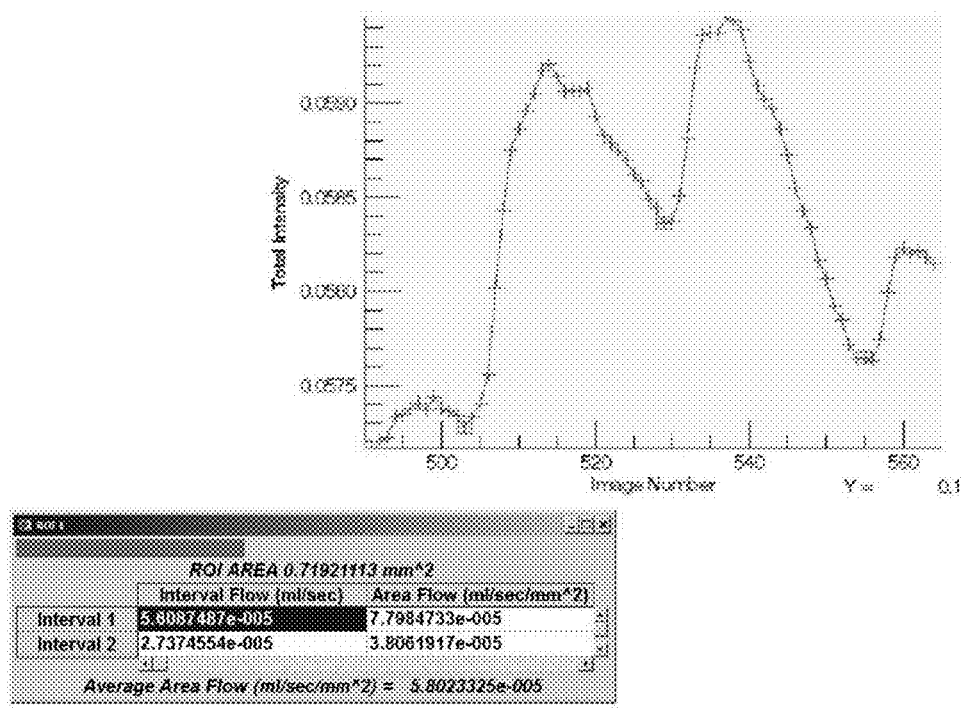
FIG. 16 shows validation data from a Rhesus monkey eye, and in particular, a plot generated for images 490-565, wherein the valleys between two consecutive blood flow pulses are selected (squares); the table indicates computed blood flow for each pulse as well as average flow.
Figure 17:
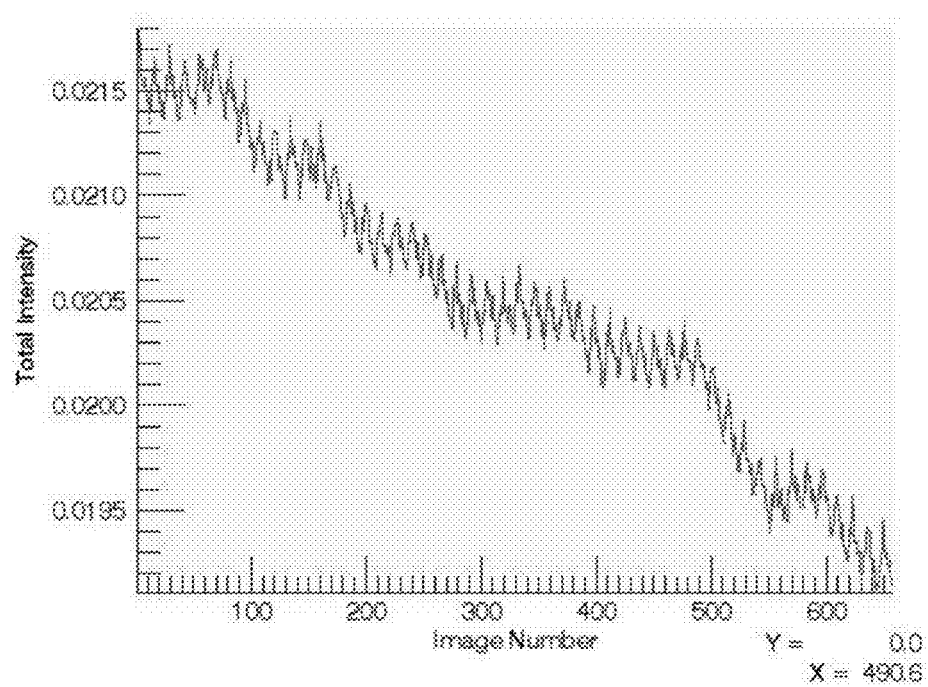
FIG. 17 shows a second angiogram sequence in connection with validation data from a Rhesus monkey eye.

A second plot was generated for images 490-565 was generated, and the valleys between two consecutive blood flow pulses were selected (green squares). At the same time, a table indicating computed blood flow for each pulse, as well as average flow (0.058 µL/sec/mm$^2$) was also generated as is shown in FIG. 16. Generally, the same procedure was followed for the second angiogram sequence shown in FIG. 17. From this plot, the subset of images 300-381 was selected, and the corresponding ICG dye concentration (C) was calculated based on the intensity of the pulses in this subset (0.0204), compared to the intensity of the peak brightness in the first sequence (0.0595, which corresponded to a 148 µM concentration). Thus, 148 µM/0.0595=C/0.0204, so C=50.7 µM.

Figure 18:
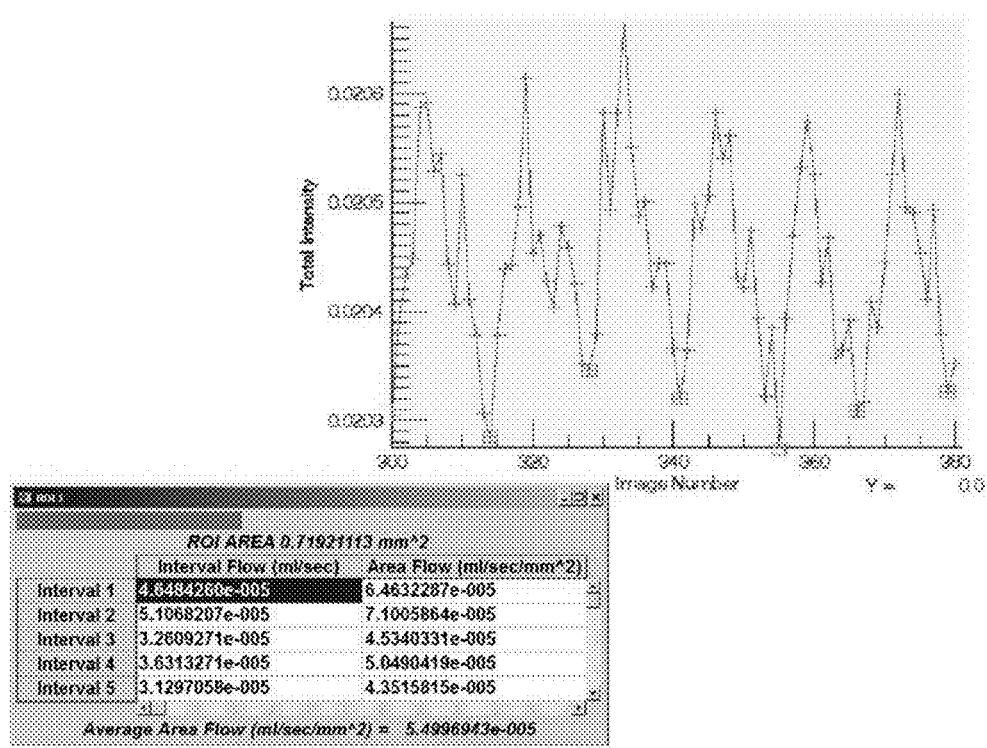
FIG. 18 shows a plot generated for images 300-381, wherein the valleys between five consecutive blood flow pulses are selected (squares); the table indicates computed blood flow for each pulse, as well as average flow.
Figure 19:
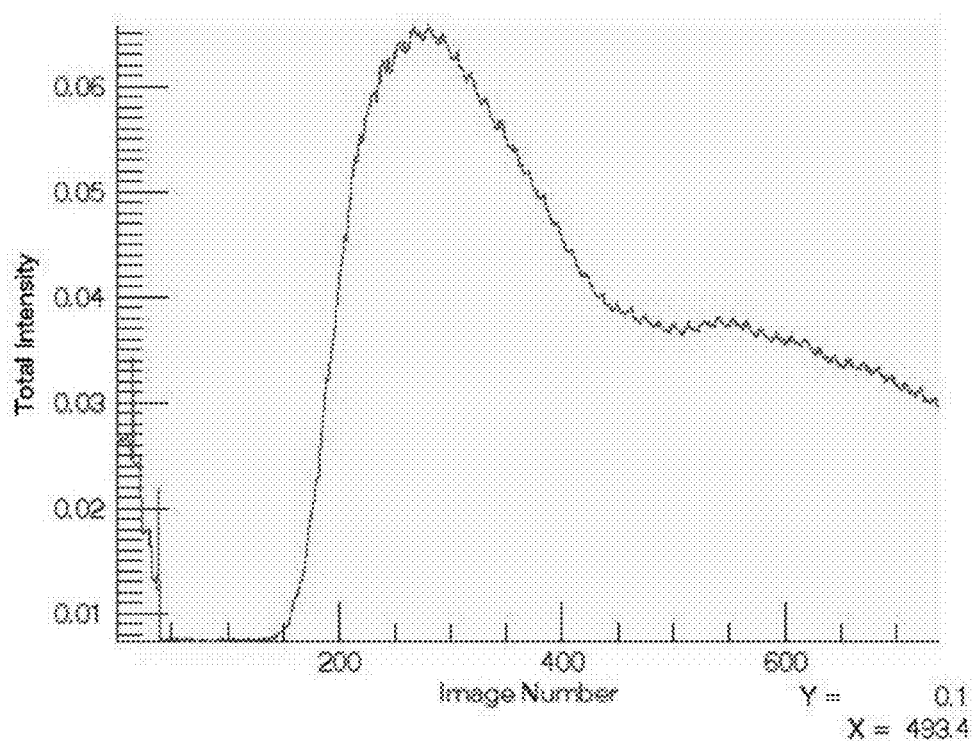
FIG. 19 shows a third angiogram sequence in connection with validation data from a Rhesus monkey eye.

The second plot was generated for images 300-381 was generated, and the valleys between five consecutive blood flow pulses were selected (squares). At the same time a table indicating computed blood flow for each pulse, as well as average flow (0.055 µL/sec/mm$^2$) was also generated as is shown in FIG. 18. Finally, the same procedure was applied to the third sequence, yielding the plots and table, wherein the plot is shown is FIG. 19.

Again, from that plot, it was determined the subsequence of images 260-290 were at peak brightness, and the concentration of ICG in circulating blood after dilution in transit was calculated. This time, the concentration of the ICG bolus injected was 25 mg/0.5 ml=50.0 mg/ml, which was diluted by 310 times, to a concentration of 0.161 mg/ml during its transit to the eye. Therefore, the peak concentration of dye in the ocular vessels (corresponding to images 260-290) was 207 µM.

Figure 20:
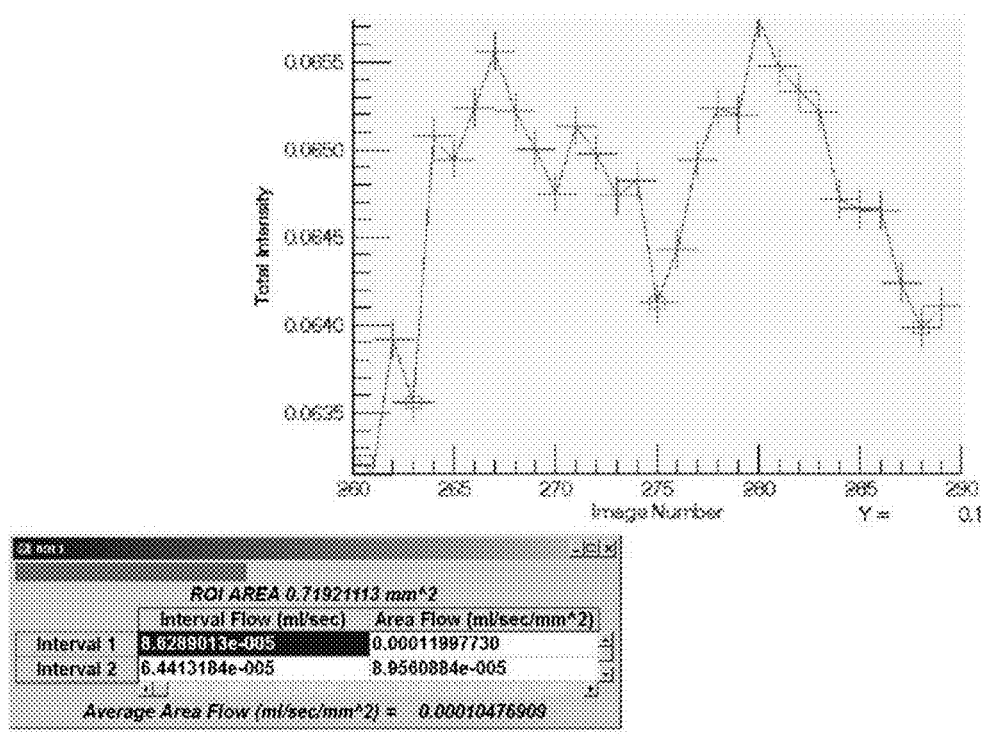
FIG. 20 shows a plot generated for images 260-290, wherein the valleys between two consecutive blood flow pulses are selected (squares); the table indicates computed blood flow for each pulse, as well as average flow.

The second plot was generated for images 260-290 was generated, and the valleys between two consecutive blood flow pulses were selected (green squares). At the same time the table indicating computed blood flow for each pulse, as well as average flow (0.105 µL/sec/mm$^2$) was also generated as is shown in FIG. 20.

The above analysis of three consecutive angiograms from the same eye yielded choroidal blood flows of 0.058, 0.055, and 0.105 µL/sec/mm$^2$, all of which compare favorably with the gold standard flow of 0.0866 µL/sec/mm$^2$, as reported by Alm and Bill and described in the following last section.

Radiolabled Microsphere Data from Cynomolgus Monkey Eyes ("Gold Standard")

The left-hand image in FIG. 21 (FIG. 21A) is an image from the human eye angiogram. In the right-hand image (FIG. 21B), the retinal area shown in the left-hand image (FIG. 21A) is represented as a box superimposed upon the autoradiograph of a flat-mounted choroid from the left eye of one of the monkeys used by Alm and Bill in their experiments. The hole in the middle is due to the removal of the optic nerve. The black spots represent the trapped microspheres, and the density of the spots is a measure of blood flow rate. The areas encompassed by the red box includes the foveal and peripapillary regions, which according to their results from 17 subjects, have blood flows of 6.49 and 4.53 mg/min/mm$^2$, respectively. These data translate into an average flow rate of 0.866 µL/sec/mm$^2$ for the encompassed area.

Thus, according to the various embodiments, a physical relationship is exploited between the absorption of light in a material (e.g., tissue) and the concentration of absorbents in the material, and this relationship is used as means to quantify blood flow. According to the various embodiments, because all of the variables discussed above can be independently determined, from such a determination, a change over time of absorbents can be determined (e.g., using Beer-Lambert Law also known as Beer's law, the Lambert-Beer law, or the Beer-Lambert-Bouguer law) to give a representation of the blood flow (absolute blood flow). In various embodiments, the Beer-Lambert Law is applied to using a fluorescence dye (wherein the fluorescence gives an indication of absorption) as an indication of the concentration of the fluorescence dye in blood using time as a measure of blood flow.

In various embodiments, all of the variables discussed above are independently determined. However, the most difficult aspect relates to the determination of the instantaneous concentration of blood at any time. The fluorescence dye such as ICG changes its spectrum slightly with concentration. According to various embodiments, examples of approaches to determine the instantaneous concentration include using a fluorescence ratio. For example, a ratio of two different wavebands may be used. According to an embodiment, two different wavelength bands could bracket the wavelength band of interest (i.e., the band used to perform the imaging), and the fluorescence is split into three bands. In various embodiments, the low signal limitation may be addressed by taking two wavelength bands for determination of the fluorescence ratio and at the same time using the whole spectrum to image (e.g., time multiplexing). In various other embodiments, instead of looking at fluorescence, an assessment can be made by looking at the absorption of the fluorescence dye. In this embodiment, a higher signal may be detected.

While the present invention has been illustrated and described in connection with various embodiments shown and described in detail, it is not intended to be limited to the details shown, since various modifications and structural changes may be made without departing in any way from the scope of the present invention. Various modifications of form, arrangement of components, steps, details and order of operations of the embodiments illustrated, as well as other embodiments of the invention may be made without departing in any way from the scope of the present invention, and will be apparent to a person of skill in the art upon reference to this description. It is therefore contemplated that the appended claims will cover such modifications and embodiments as they fall within the true scope of the invention.

What is claimed is:

1. A method for measuring a time-varying change in an amount of blood in a tissue volume of tissue of a subject, comprising:

administering a fluorescence agent into vasculature supplying the tissue volume of tissue of the subject;

exciting a fluorescence agent in the blood, the fluorescence agent having an instantaneous molar concentration in the blood;

capturing a sequence of fluorescence images of the tissue;

acquiring, from the sequence of fluorescence images of the tissue, a time-varying fluorescence intensity signal emitted by the fluorescence agent during a pulsatile flow of the blood through the tissue volume, wherein:

the pulsatile flow has a diastolic and a systolic phase resembling a conventional photoplethysmogram, the acquired fluorescence intensity signal comprises a first fluorescence intensity emitted by the fluorescence agent in the blood in the tissue volume during a diastolic phase minimum, the acquired fluorescence intensity signal comprises a second fluorescence intensity emitted by the fluorescence agent in the blood in the tissue volume during a systolic phase maximum, and the first and second fluorescence intensities are respectively associated with measures of blood volume during the diastolic phase and the systolic phase; and computing a change in an aggregate blood layer thickness in the tissue volume based on the first and second fluorescence intensities, wherein the change represents a quantitative measure of tissue blood perfusion in the tissue volume; and displaying the quantitative measure to facilitate clinical assessment of the tissue of the subject.

2. The method of claim 1, wherein the fluorescence agent is indocyanine green (ICG).

3. The method of claim 2, wherein the ICG is administered at a concentration of between 25-50 mg/mL.

4. The method of claim 1, wherein the fluorescence images are obtained at a frame rate of 20-30 frames per second.

5. The method of claim 1, wherein the fluorescence images are obtained by a fluorescence imaging system.

6. The method of claim 5, wherein the fluorescence imaging system comprises a laser for excitation of the ICG and a camera for capturing images of the fluorescence emitted by the ICG.

7. The method of claim 1, wherein aggregate blood flow, F, is derived according to the formula:

$$F=(A)(\Delta L)(P_{DC})/\Delta t,$$

wherein

A is a cross-sectional area of the tissue volume end, $\Delta L$ is the derived change in the aggregate blood layer thickness, $P_{DC}$ is a pulse duty cycle, and $\Delta t$ is a duration of a single pressure pulse.

8. The method of claim 1, wherein the fluorescence imaging protocol further comprises administering a saline flush, following administering the fluorescence agent, to achieve a circulating peak dye concentration in excess of a predefined molar concentration.

9. The method of claim 1, further comprising:

acquiring additional fluorescence wavelength data simultaneously with obtaining the fluorescence images; and using the additional fluorescence wavelength data for dual-wavelength ratiometric analysis for determining an intravascular concentration of the imaging agent.

10. The method of claim 9, wherein acquiring additional fluorescence wavelength data comprises:

measuring a fluorescence intensity signal from a first wavelength range longer than the wavelength range used for the fluorescence imaging; and measuring a fluorescence intensity signal from a second wavelength range longer than the wavelength range used for the fluorescence imaging.

11. The method of claim 10, wherein the first wavelength range and the second wavelength range are within the near infrared spectrum.

* * * * *